(12) United States Patent
Wiederin et al.

(10) Patent No.: US 9,341,229 B1
(45) Date of Patent: May 17, 2016

(54) AUTOMATED SAMPLING DEVICE

(71) Applicant: Elemental Scientific, Inc., Omaha, NE (US)

(72) Inventors: Daniel R. Wiederin, Omaha, NE (US); David Diaz, Omaha, NE (US); Gary J. Barrett, Omaha, NE (US)

(73) Assignee: Elemental Scientific, Inc., Omaha, NE (US)

( * ) Notice: Subject to any disclaimer, the term of this patent is extended or adjusted under 35 U.S.C. 154(b) by 324 days.

(21) Appl. No.: 14/022,444

(22) Filed: Sep. 10, 2013

Related U.S. Application Data

(60) Provisional application No. 61/698,933, filed on Sep. 10, 2012.

(51) Int. Cl.
*G01N 35/10* (2006.01)
*F16F 15/03* (2006.01)
*G01N 1/00* (2006.01)

(52) U.S. Cl.
CPC . *F16F 15/03* (2013.01); *G01N 1/00* (2013.01)

(58) Field of Classification Search
None
See application file for complete search history.

(56) References Cited

U.S. PATENT DOCUMENTS

| | | |
|---|---|---|
| 3,022,718 A | 2/1962 | Thompson |
| 4,311,667 A | 1/1982 | Gocho |
| 4,529,403 A | 7/1985 | Kamstra |
| 4,767,413 A | 8/1988 | Haber et al. |
| 4,822,340 A | 4/1989 | Kamstra |
| 4,841,786 A | 6/1989 | Schulz |
| 4,888,998 A | 12/1989 | Buzza et al. |
| 4,926,746 A | 5/1990 | Smith |
| 5,270,211 A | 12/1993 | Kelln et al. |
| 5,331,840 A | 7/1994 | Williams |
| 5,364,596 A | 11/1994 | Magnussen et al. |
| 5,464,029 A | 11/1995 | Rentz |
| 5,479,969 A | 1/1996 | Hardie et al. |
| 5,501,984 A | 3/1996 | Hofstetter et al. |
| 5,527,296 A | 6/1996 | Kashanchi |
| 5,860,711 A | 1/1999 | Kronberg et al. |
| 5,876,668 A | 3/1999 | Kawashima et al. |
| 5,879,944 A | 3/1999 | Komatsu |
| 6,001,309 A | 12/1999 | Gamble et al. |
| 6,028,525 A | 2/2000 | Shukla et al. |
| 6,148,680 A | 11/2000 | Baeuerle et al. |
| 6,203,760 B1 | 3/2001 | van der Plaats et al. |
| 6,349,654 B1 | 2/2002 | Peters |
| 6,595,247 B1 | 7/2003 | Landy et al. |
| 6,637,476 B2 | 10/2003 | Massaro |
| 6,866,820 B1 | 3/2005 | Otto et al. |

(Continued)

*Primary Examiner* — Robert R Raevis
(74) *Attorney, Agent, or Firm* — Advent, LLP

(57) ABSTRACT

A dampening device for an automated sampling/dispensing device is described. In an example implementation, the dampening device includes a cylindrical body. The cylindrical body includes a first end and a second end, a first opening being defined within the first end and a second opening being defined within the second end. Further, the cylindrical body may include an inner diameter greater than an outer diameter of an automated sampling/dispensing device sample probe. During operation, the dampening device moves out of phase with the automated sampling/dispensing device sample probe allowing sample probe vibrations to be dampened during operation. The dampening device is configured to be magnetically attracted to the sampling/dispensing device. For example, the dampening device and/or the sampling/dispensing device can include a permanent magnetic material, a ferromagnetic material, a ferrimagnetic material, and/or an electromagnet.

13 Claims, 24 Drawing Sheets

(56) References Cited

U.S. PATENT DOCUMENTS

| | | |
|---|---|---|
| 7,201,072 B1 | 4/2007 | Wiederin et al. |
| 7,469,606 B1 | 12/2008 | Wiederin |
| 7,637,175 B1 | 12/2009 | Wiederin et al. |
| 7,690,275 B1 | 4/2010 | Wiederin et al. |
| 2002/0106814 A1 | 8/2002 | Matsubara et al. |
| 2002/0177788 A1 | 11/2002 | Hodges et al. |
| 2003/0077203 A1 | 4/2003 | Gudmundsson et al. |
| 2003/0090174 A1 | 5/2003 | Ryder |
| 2003/0143123 A1 | 7/2003 | Maeda |
| 2003/0143748 A1 | 7/2003 | Gudmundsson et al. |
| 2003/0143749 A1 | 7/2003 | Gudmundsson et al. |
| 2003/0147778 A1 | 8/2003 | Takahashi |
| 2003/0180188 A1 | 9/2003 | Michael et al. |
| 2004/0018119 A1 | 1/2004 | Massaro |
| 2004/0126283 A1 | 7/2004 | Backes et al. |
| 2004/0146433 A1 | 7/2004 | Massaro |
| 2005/0059164 A1 | 3/2005 | Feygin |
| 2005/0095724 A1 | 5/2005 | Shibutani et al. |
| 2006/0074349 A1 | 4/2006 | Fan |
| 2006/0088940 A1 | 4/2006 | Feingold et al. |
| 2006/0120922 A1 | 6/2006 | Matsumoto |

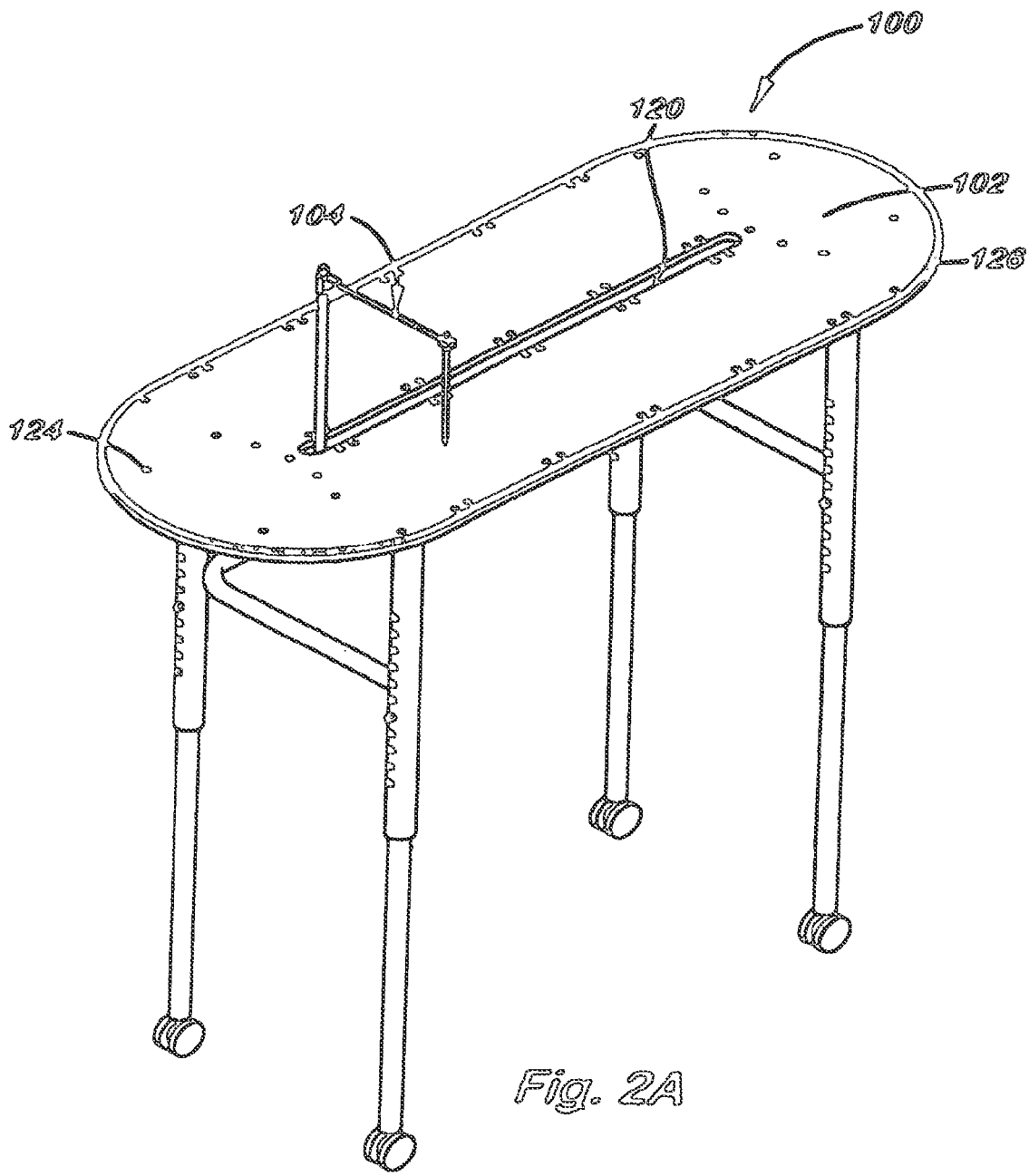

AUTOMATED SAMPLING DEVICE

CROSS-REFERENCE TO RELATED APPLICATIONS

The present application claims the benefit of 35 U.S.C. §119(e) of U.S. Provisional Application Ser. No. 61/698,933, filed Sep. 10, 2012, and titled "AUTOMATED SAMPLING DEVICE," which is herein incorporated by reference in its entirety.

BACKGROUND

In many laboratory settings, it is often necessary to analyze a large number of chemical or biochemical samples at one time. In order to stream-line such processes, the manipulation of samples has been mechanized. Such mechanized sampling is commonly referred to as autosampling and is performed using an automated sampling device or autosampler.

SUMMARY

A dampening device for an automated sampling/dispensing device is described. The dampening device includes a cylindrical body. The cylindrical body includes a first end and a second end, a first opening being defined within the first end and a second opening being defined within the second end. Further, the cylindrical body may include an inner diameter greater than an outer diameter of an automated sampling/dispensing device sample probe. During operation, the dampening device moves out of phase with the automated sampling/dispensing device sample probe allowing sample probe vibrations to be dampened during operation. The dampening device is configured to be magnetically attracted to the sampling/dispensing device. For example, the dampening device and/or the sampling/dispensing device can include a permanent magnetic material, a ferromagnetic material, a ferrimagnetic material, and/or an electromagnet.

A dampening device for an automated sampling/dispensing device is provided. The dampening device includes a body. The body may include a plurality of walls, a first end and a second end. Further, a first opening is defined within the first end and a second opening is defined within the second end for allowing the body to be positioned around an automated sampling/dispensing device sample probe. Additionally, the body includes an inner diameter greater than an outer diameter of the automated sampling/dispensing device sample probe. The dampening device is positioned around the automated sampling/dispensing device sample probe so that during operation the device moves out of phase with the automated sampling/dispensing device sample probe allowing sample probe vibrations to be dampened. The dampening device is configured to be magnetically attracted to the sampling/dispensing device. For example, the dampening device and/or the sampling/dispensing device can include a permanent magnetic material, a ferromagnetic material, a ferrimagnetic material, and/or an electromagnet.

An automated sampling/dispensing device including a dampening device is provided. The automated sampling/dispensing device includes a support surface for supporting a sample holder. The sample holder is configured for holding a sample vessel. Further, a sample arm assembly for supporting a sample probe is included in which such assembly includes a z-axis support and a sample probe support arm. Additionally, a drive assembly is coupled to the z-axis support of the sample arm assembly for powering and positioning the sample arm assembly so that the drive assembly causes the sample arm assembly to move in translation along the x-axis, in translation along an axis coaxial with the z-axis support, and radially about the z-axis. Moreover, a dampening device is operationally coupled to the sample arm assembly for dampening vibrations of the sample arm assembly during operation. The dampening device includes a cylindrical body. The cylindrical body includes a first end and a second end with a first opening being defined within the first end and a second opening being defined within the second end for allowing the cylindrical body to be positioned around the sample probe. In addition, the cylindrical body includes an inner diameter greater than an outer diameter of the sample probe. The dampening device is positioned around the sample probe so that during operation the dampening device moves out of phase with the sample probe allowing sample probe vibrations to be dampened. The dampening device is configured to be magnetically attracted to the sampling/dispensing device. For example, the dampening device and/or the sampling/dispensing device can include a permanent magnetic material, a ferromagnetic material, a ferrimagnetic material, and/or an electromagnet.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

DRAWINGS

The Detailed Description is described with reference to the accompanying figures. The use of the same reference numbers in different instances in the description and the figures may indicate similar or identical items.

FIG. 2A is a partial isometric view illustrating an automated sampling or dispensing device in accordance with example implementations of the present disclosure, where a center slot in the support surface is present allowing the sample arm assembly to be connected with the drive assembly.

DETAILED DESCRIPTION

Figure 1:
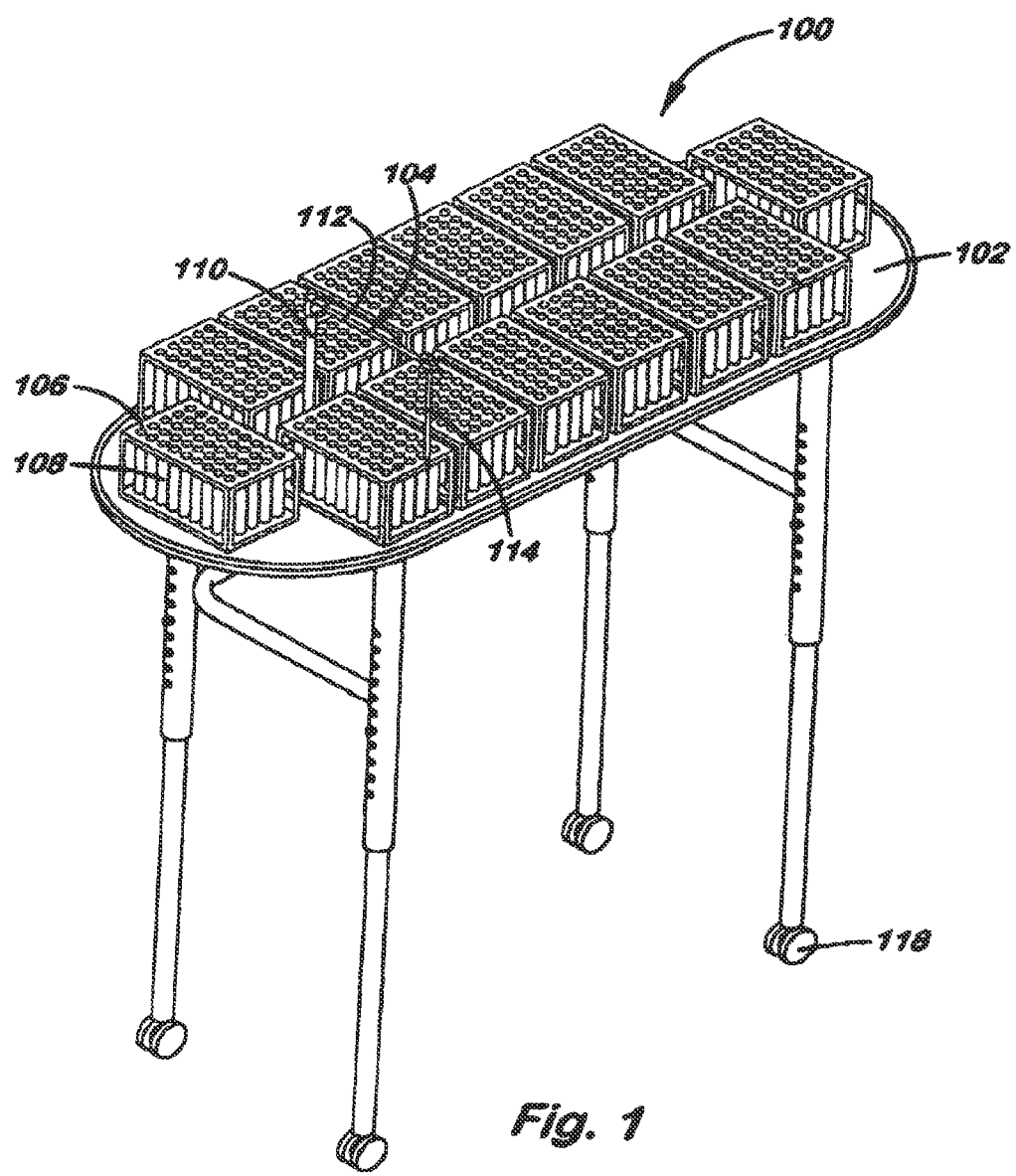
FIG. 1 is an isometric view illustrating an automated sampling or dispensing device in accordance with example implementations of the present disclosure.

FIG. 1 illustrates automated sampling device 100 in accordance with an example implementation of the present disclosure. Automated sampling device 100 includes table top 102 and sample arm assembly 104. Further, sample holders 106 holding multiple sample vessels 108 are present on table top 102 in preparation for sample assaying. It should be understood that automated sampling device 100 may assay from one to many hundreds of samples (e.g., greater than 1200 samples in the example implementation illustrated) in a given time depending upon test requirements.

In the implementation illustrated, sample arm assembly 104 includes a z-axis support 110 and a sample probe support arm 112 that supports a sample probe 114. As illustrated, the z-axis is aligned with gravity or a vertical axis. In use, sample probe 114 is mounted to sample probe support arm 112, which is moved through space in three dimensions, or about an axis having y-motion that is a substantially rotary motion and along an axis having x-motion which is at least substantially horizontal linear motion or translation, and along a z-axis that is at least substantially vertical, for linear motion or translation. In an implementation, the length of a sample probe support arm (the length of an arm extending from the y-rotary axis) is no more than one-half the length of a linear translation of the center slot (i.e., is no more than half of the length of x-axis linear motion). In an implementation, the length of the sample probe support arm is approximately equal to one-half the length of a linear translation of the center slot. Such configuration allows nearly one hundred percent of the footprint of the table to be accessed by the sample probe. Footprint is defined as being substantially equivalent to an area encompassed by the area of the table top. In an additional implementation, the y-rotary axis of an automated sampling device allows for access to sample vessels on either side of the x-axis motion of linear travel (i.e., on either side of the center slot).

In an implementation, the components of sample arm assembly 104 are formed of carbon composite materials. Further, all exposed surfaces of the sample arm assembly 104 are made from inert or fluoropolymer-covered materials (i.e., Teflon®). It should be understood, however, that the sample arm assembly may be made with various materials, including aluminum, steel, plastic, and so forth.

In addition, sample arm assembly 104 is designed to attach to various surface supports including a table top. Such assembly may be attached to either side of the center slot. In an implementation, table top 102 may be mounted onto legs with casters 118, rollers and so forth. Such configuration increases the mobility of the automated sampling device, thereby facilitating preparation of samples at a location separate from the analytical instruments. Further, this configuration provides storage room underneath the table top which may be absent with bench-top automated sampling devices. The height of the table is adjustable to compensate for the effects of gravity on liquid flow rates when self-aspirating sampling devices are used. The ability to adjust table top height also allows the automated sampling device to accommodate various sized sample vessels.

Figure 2B:
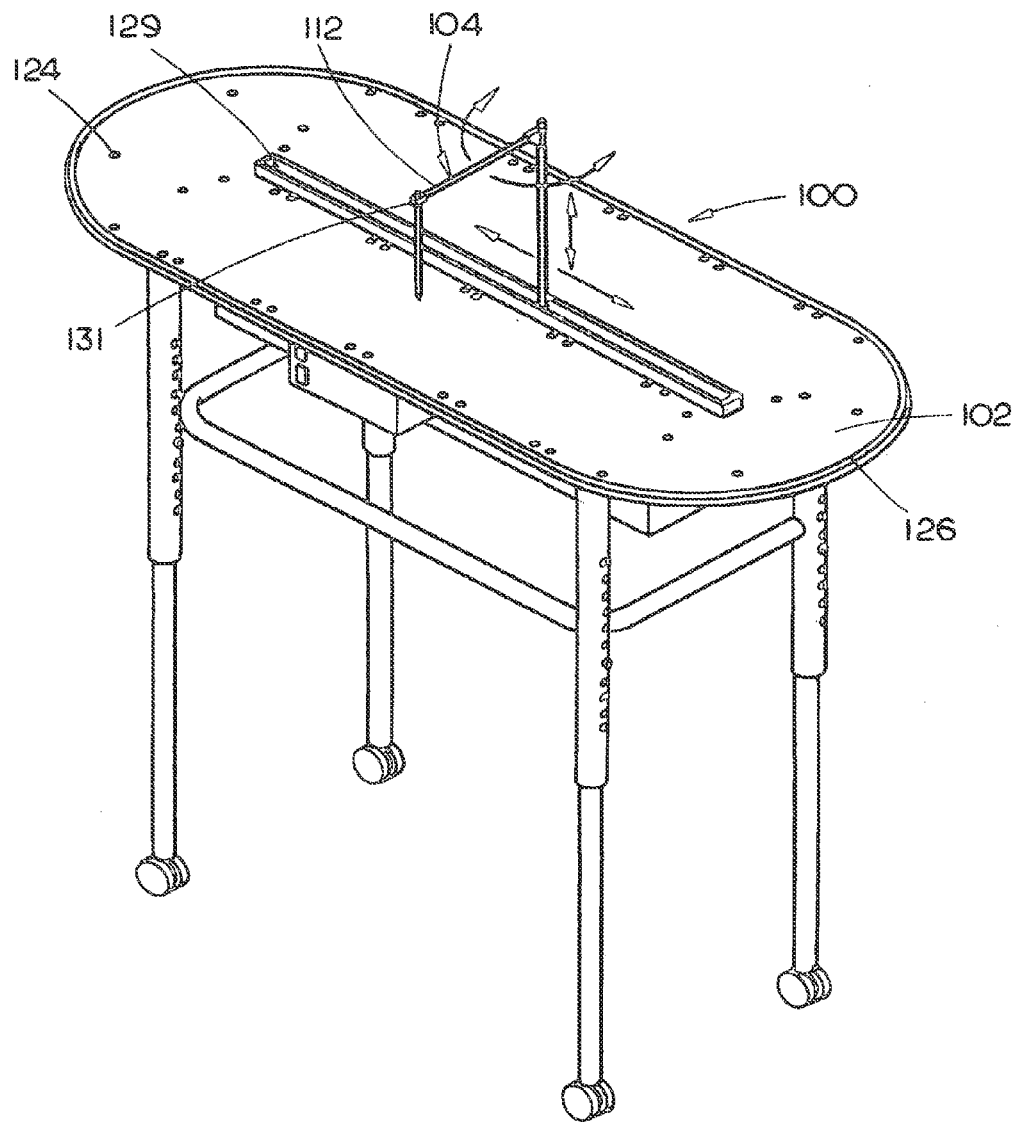
FIG. 2B is a partial isometric view illustrating an automated sampling or dispensing device in accordance with example implementations of the present disclosure, where a raised slot on the support surface is present to attach the sample arm assembly to the drive assembly.

FIGS. 2A and 2B are additional illustrations of automated sampling or dispensing devices in which the sample arm assembly is attached to the drive assembly via a center slot or a raised slot, respectively. In FIG. 2A, automated sampling device 100 is comprised of sample arm assembly 104 extending through center slot 120 and table top 102 including a plurality of recesses 124 and the channel 126. The sample arm assembly 104 is attached to the drive assembly (not shown) via center slot 120. In an implementation, the plurality of recesses is coupled with sensors for detecting the location of sample holders. The sample holder location information may then be transferred to a controller of a drive assembly controlling the sample arm assembly providing the alignment system. The previous configuration allows the sample arm assembly to detect the location of sample vessels on the table top at a given time. Channel 126 runs along the edge of table top 102 to collect possible sample spillage.

In addition to FIG. 2A, FIG. 2B demonstrates an automated sampling or dispensing device including a sample arm assembly 104 attached to the drive assembly 128 via a raised slot 129. In one implementation, a magnet 131 is attached to the end of the sample probe support arm 112 which allows detection of a three-dimensional position in space where the magnet 131 is embedded into the sample probe support arm 112 and is detected by a sensing means such as a Hall Effect sensor.

Figure 3:
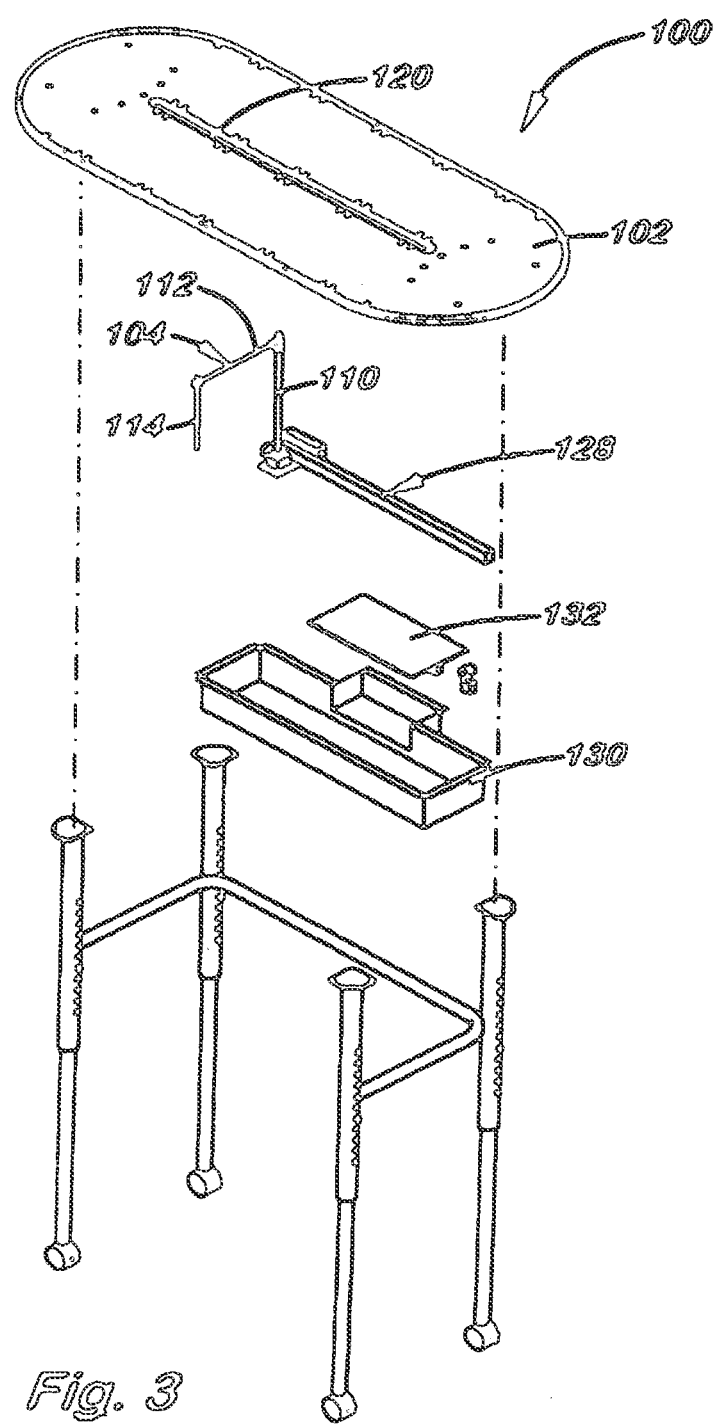
FIG. 3 is an exploded view of the automated sampling or dispensing device shown in FIG. 1, further illustrating components of the device.

Referring now to FIG. 3, an exploded view of the components comprising the automated sampling device 100 is provided. The automated sampling device 100 is comprised of a table top 102 with center slot 120, drive assembly 128, sample arm assembly 104, housing 130, and controller 132. Sample arm assembly 104 includes z-axis support 110 attached to drive assembly 128, sample probe support arm 112 attached to z-axis support 110, and sample probe 114 attached to sample probe support arm 112. Sample arm assembly 104 is controlled by drive assembly 128 and controller 132. In an implementation, drive assembly 128 causes sample arm assembly 104 to move along center slot 120, in translation along an axis coaxial to z-axis support 110, and radially about the z-axis for inserting sample probe 114 into a sample vessel. Further, sample arm assembly 104 is no more than one-half the length of a linear translation of the length of center slot 120. As previously mentioned, such configuration allows nearly one hundred percent of the footprint to be accessed by sample probe 114. In addition, automated sampling device 100 is capable of assaying hundreds of samples at a given time without operator assistance, thereby allowing the operator to perform other tasks. Moreover, it is possible to configure the automated sampling device to assay samples overnight, allowing work productivity to be increased.

To accommodate gross differences in sample vessel height, sample probe support arm 112 may be moved up or down z-axis support 110 as desired prior to sample assaying. Once the desired position is reached, sample probe support arm 112 is secured into a fixed position on z-axis support 110 and sample vessels containing samples may be loaded onto the table top. This feature allows the automated sampling device to be used on various sizes of sample vessels while still not having mechanical moving parts above stationary samples. Additionally, housing 130 encloses drive assembly 128 to protect the assembly from debris, dust, contaminates, and so forth. Housing 130 may be made of various materials, e.g., blow molded polyethylene, and so forth.

Figure 4A:
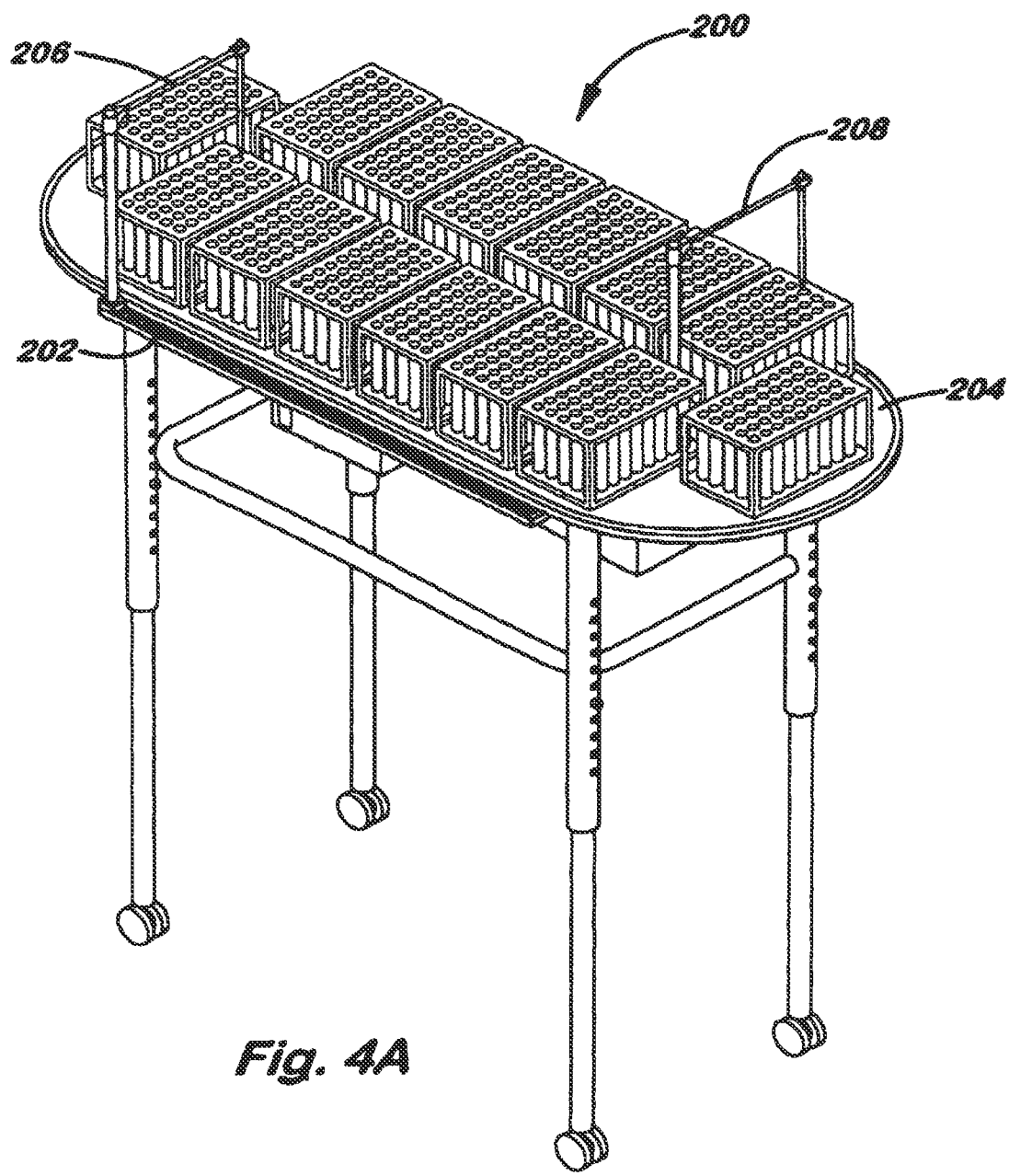
FIG. 4A is an isometric view illustrating an automated sampling or dispensing device in accordance with example implementations of the present disclosure where multiple sampling arm assemblies and drive assemblies are mounted to the top of the support surface of the automated sampling or dispensing device.
Figure 4B:
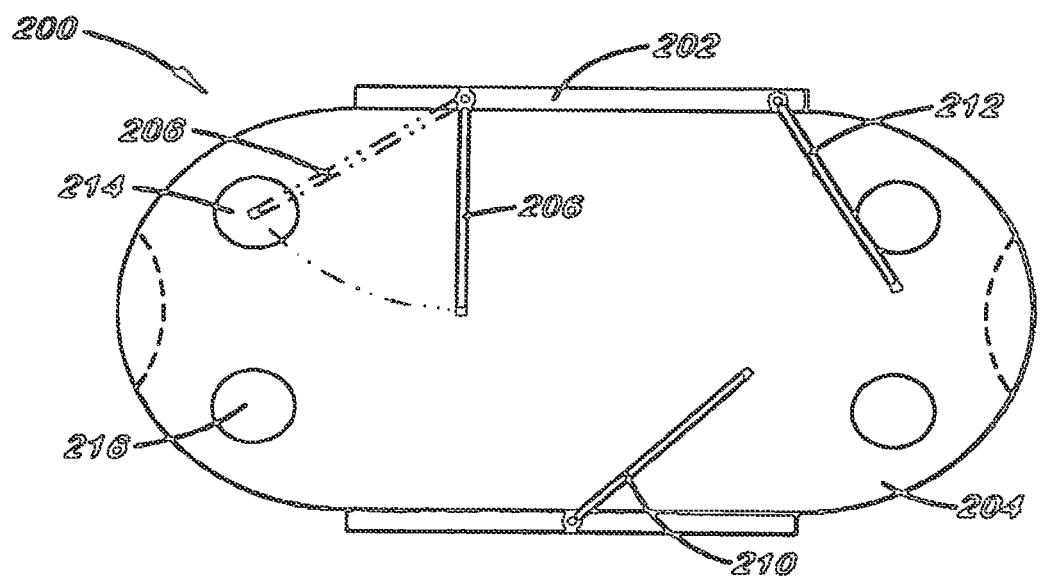
FIG. 4B is a plan view illustrating an automated sampling or dispensing device in accordance with example implementations of the present disclosure, where multiple sample arm assemblies and rinse stations are present on one support surface.

FIGS. 4A and 4B illustrate an automated sampling device 200 in accordance with another example implementation of the present disclosure, where multiple sampling arm assemblies (i.e., sample arm assembly 206, 208, and 210) are mounted to the table top of the automated sampling device. Automated sampling device 200 includes multiple automated sampling devices attached to a table top at one time. A rail 202 is attached to the edge of table top 204 to enable the attachment of additional sample arm assemblies (i.e., sample arm assembly 206 and 212). Utilization of additional sample arm assemblies allows multiple sample zones to be configured (i.e., a prep zone, an assaying zone, and so forth).

In additional implementations, various types of multiple rinse or eluent stations may be included in the automated sampling device. For instance, multiple rinse stations (i.e., 214 and 216) of the overflow type designed to reduce the chance of carry-over contamination may be present. Further, overflow rinse stations may contain a series of different chemical rinses to reduce contamination between sample analyses (e.g., surfactant, nitric acid, hydrofluoric acid, and/or deionized water). For multiple eluent stations, the automated sampling device may contain such stations for step elution from a chromatographic column.

Figure 5:
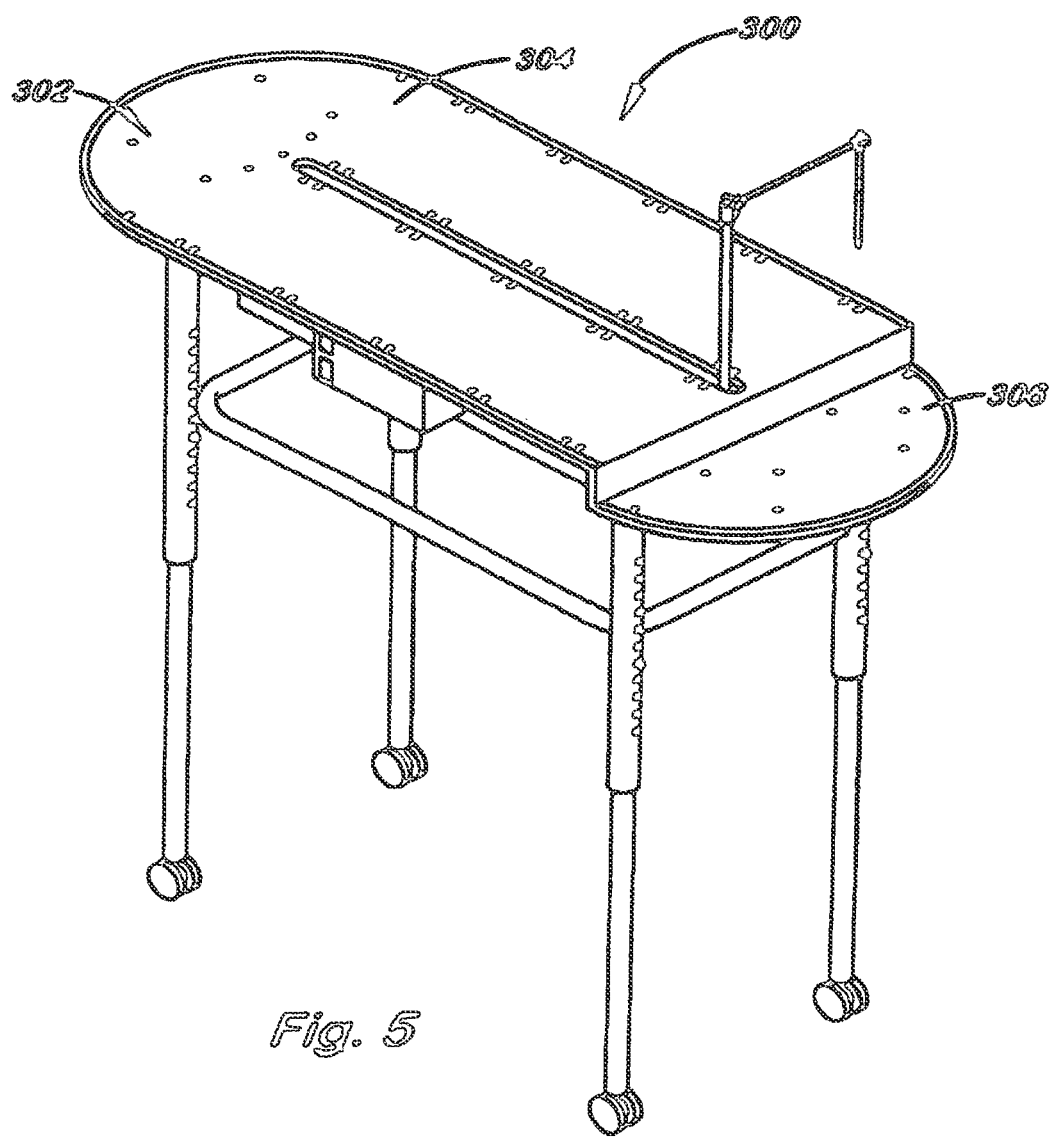
FIG. 5 is an isometric view illustrating an automated sampling or dispensing device in accordance with example implementations of the present disclosure, where the support surface of the automatic sampling or dispensing device is provided with more than one plane.

Referring now to FIG. 5, an automated sampling device in accordance with another example implementation of the present disclosure is described, where a table top having more than one plane is provided. Automated sampling device 300 includes table top 302 which has more than one plane, plane one 304 and plane two 306. Such configuration allows table top 302 to accommodate various sizes of vessels. For instance, the height of vessels in plane two 306 may be taller than vessels in plane one 304 of table top 302.

Figure 6:
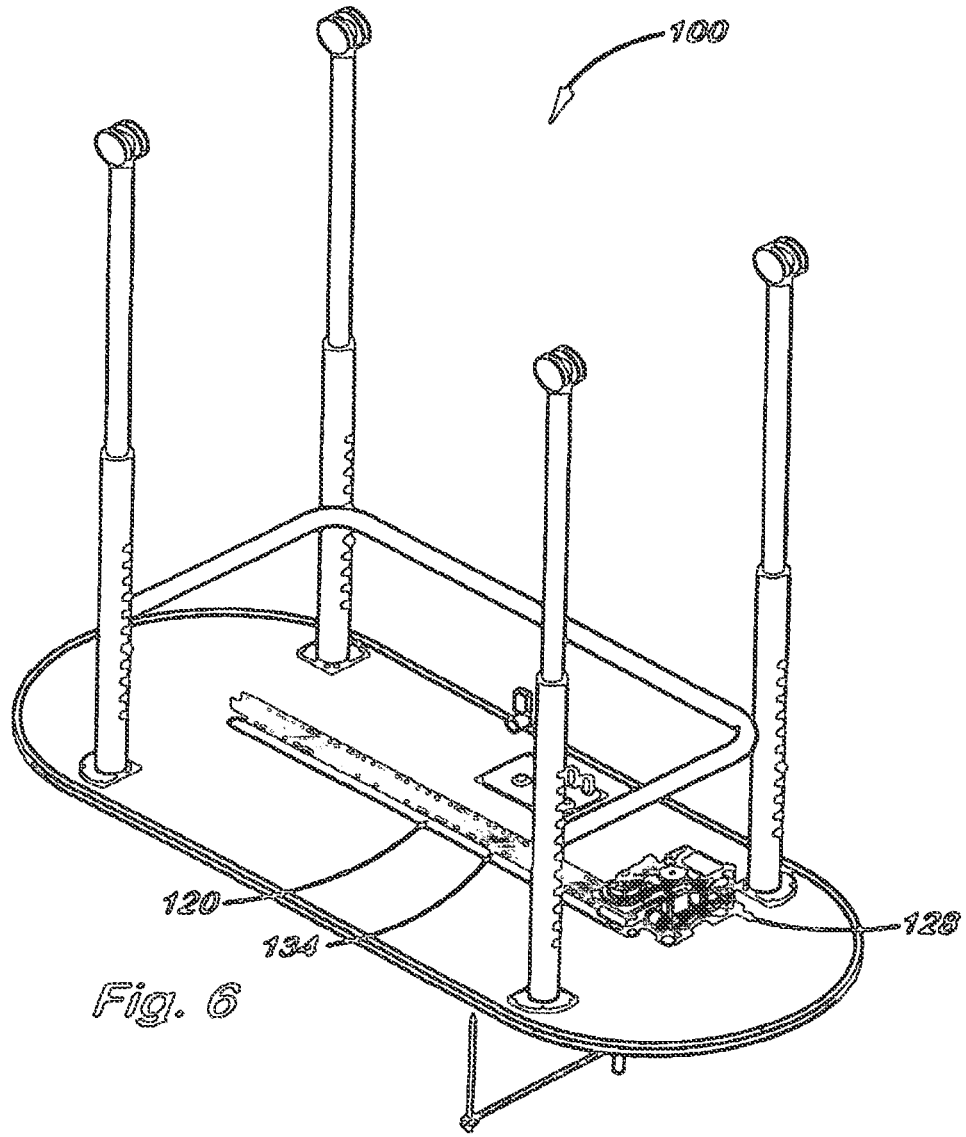
FIG. 6 is an isometric view of the automated sampling or dispensing device shown in FIG. 1, further illustrating the drive assembly.
Figure 7:
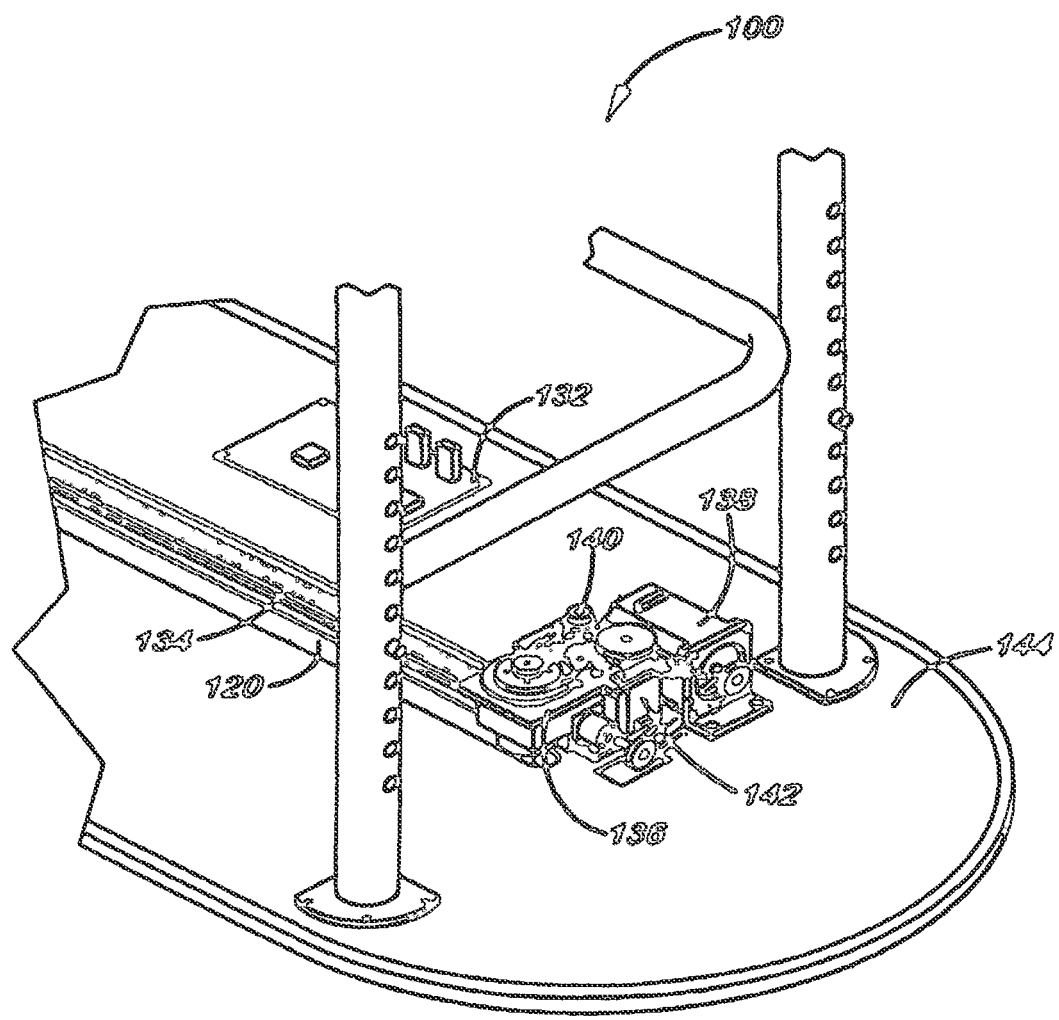
FIG. 7 is a partial isometric view of the drive assembly shown in FIG. 6, further illustrating components of the drive assembly.

FIGS. 6 and 7 further illustrate a drive assembly of automated sampling device 100 attached to a table top bottom. FIG. 6 provides an overview of a drive assembly in accordance with the present disclosure, depicting a linear drive 134 running parallel to center slot 120 and connected to sled 128. FIG. 7 is an enlarged view of the drive assembly illustrated in FIG. 6. Drive assembly 100 is comprised of motor one 138, motor two 140, motor three 142, sled 136, linear drive 134, and controller 132. Motor one 138 controls translation of a sample arm assembly's movements along the center slot 120 and is attached to table top bottom 144 and linear drive 134. Various stepper motors may be used to control translation of the sample arm assembly's movements along center slot 120. Moreover, it will be appreciated that various linear drives may be used including a worm drive. Motor two 140 controls angular rotation of a sample arm assembly and is connected to sled 136. In an implementation, motor two 140 is a radial motor. Motor three 142 controls vertical movement of a sample arm assembly and is attached to sled 136. Various stepper motors may be used for controlling vertical movement of the sample arm assembly. In an additional implementation, motor three 142 comprises a slip-clutch system. Further, in accordance with the present disclosure, the drive assembly may be hard-wired or, in another implementation, controlled via wireless communication. Thus, wireless communications may be used to connect controller 132 with the desired analytical instrument (not shown). Utilization of wireless communications allows sample assaying to occur without requiring physical connection with a controller computer increasing mobility of the automated sampling device.

Figure 8:
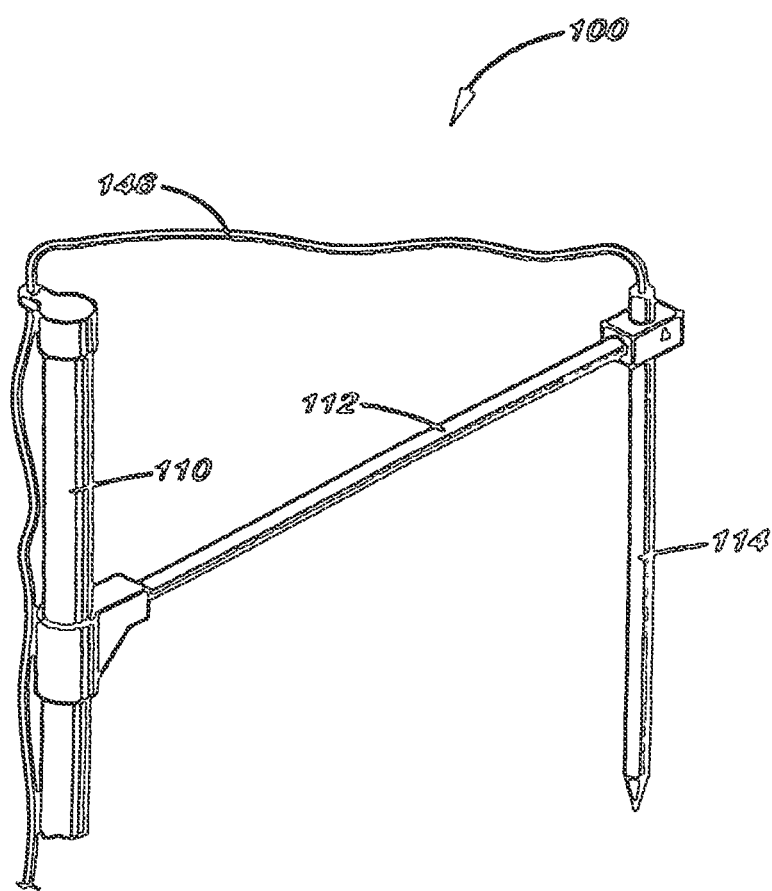
FIG. 8 is a partial isometric view illustrating a sample arm assembly for an automated sampling or dispensing device in accordance with example implementations of the present disclosure.

FIG. 8 provides a detailed depiction of a sample arm assembly of an automated sampling device in accordance with the first example implementation of the present disclosure. As previously described, the sample arm assembly includes z-axis support 110 attached to a drive assembly (see FIGS. 6 and 7), sample probe support arm 112 attached to z-axis support 110, and sample probe 114 attached to sample probe support arm 112. In an implementation, the sample arm assembly is attached to the drive assembly via the z-axis support extending through a center slot in the table top; in such implementation, the drive assembly is attached to a table top bottom. However, it should be understood that the drive assembly may be disposed in a variety of locations including on top of the table top without departing from the scope of the present disclosure.

In an additional implementation in accordance with the present disclosure, sample tubing 146 is present to allow sample removal or reagent delivery as desired. Further, a slip bearing is built into sample probe 114 to prevent winding of sample tubing 146. It is contemplated that the sample may be delivered to various types of scientific instrumentation (e.g., an inductively couple plasma system, a mass spectrometer, and so forth) or a number of other types of vessels (e.g., a waste collecting bucket following a wash step). It is further contemplated that the sample tubing may be flexible (as shown) or rigid, e.g., comprised of plastic, metal, and so forth. In another implementation, the automated sampling device may be equipped with one or more independent components for the purpose of sample preparation, sample dilution, addition of standards to samples or sample acidification.

Figure 9A:
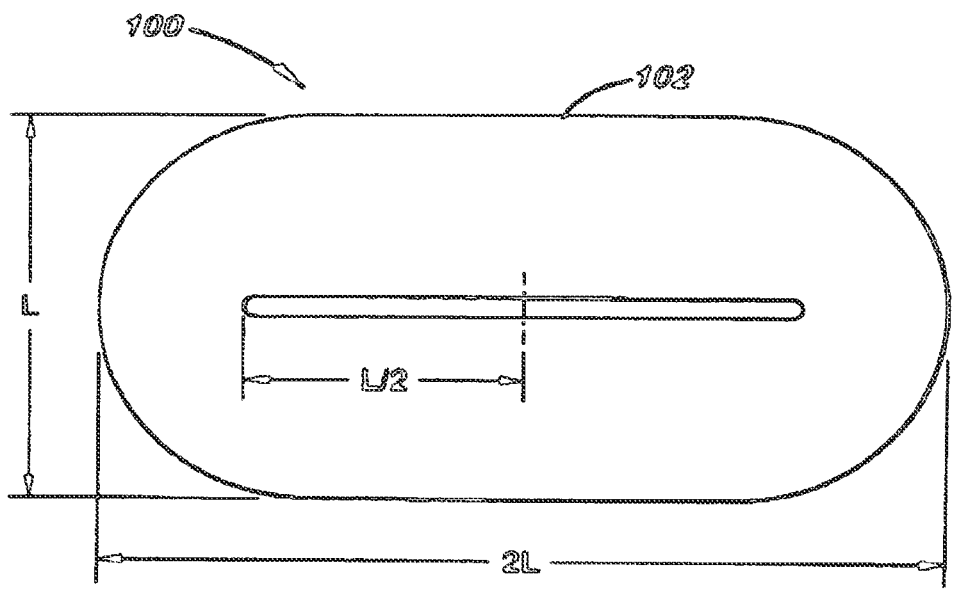
FIG. 9A is a plan view illustrating a support surface for use with an automated sampling or dispensing device, where the support surface includes a slot and has a footprint in accordance with example implementations of the present disclosure.
Figure 9B:
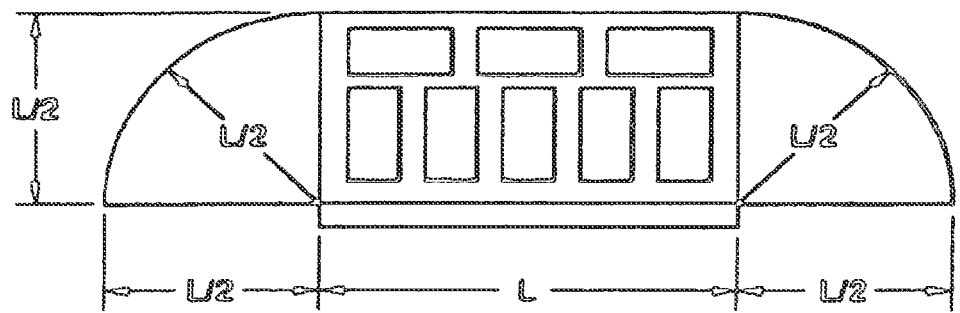
FIG. 9B is a plan view illustrating a support surface for use with an automated sampling or dispensing device, in accordance with example implementations of the present disclosure.

Referring to FIGS. 9A and 9B, tables for use with an automated sampling device are described in accordance with example implementations of the present disclosure. First, the table 102 includes a slot of length L providing for translation of the sample arm assembly along the length of the table. Further, the table 102 has a footprint for maximizing the usable area of the table 102. As illustrated in FIG. 9A, the table 102 has a width L substantially equal to the length of the slot L. Moreover, the table 102 is twice as long as the slot, having a length of 2 L. Further, the arm length of a sample probe assembly (as shown in FIGS. 1, 2, and 3) is half the length of the slot, having length L/2. This configuration allows for approximately one hundred percent of the footprint of the table to be accessed. In contrast, FIG. 9B illustrates an additional implementation in accordance with the present disclosure whereby the table is the shape of a semi-circle and a non-centered slot system is employed.

Figure 10:
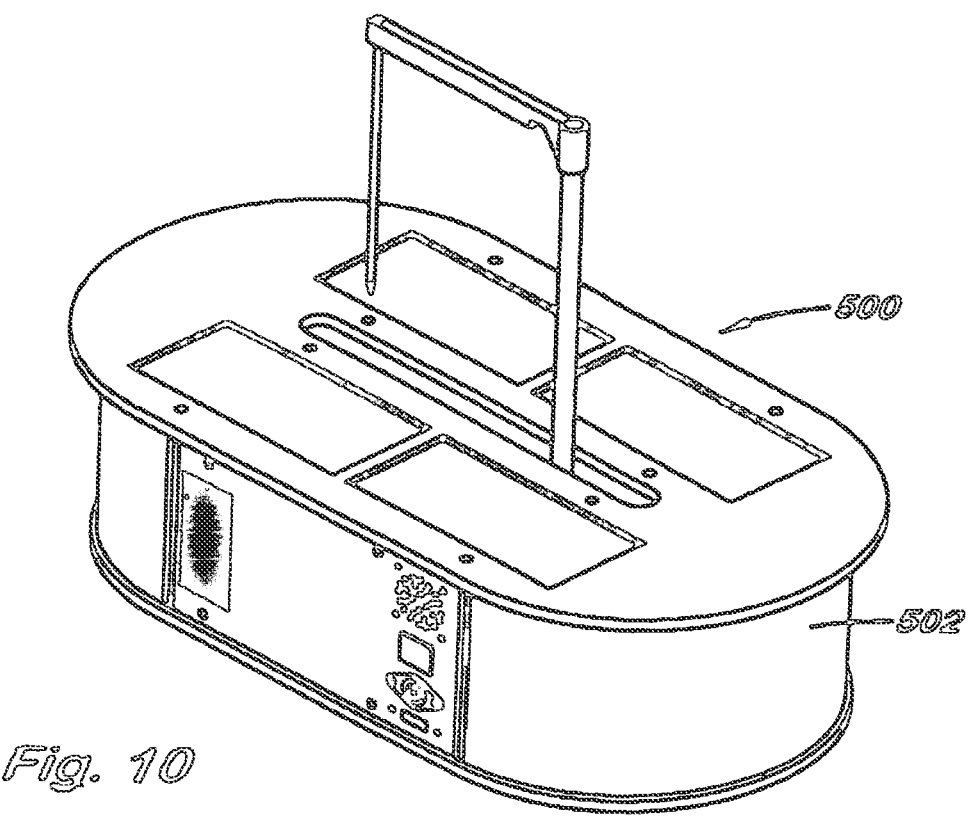
FIG. 10 is an isometric view illustrating an automated sampling or dispensing device in accordance with example implementations of the present disclosure, where the device includes a shroud.

Referring to FIG. 10, automated sampling or dispensing device 500 includes a shroud 502. In an example implementation, the shroud 502 substantially encloses the drive assembly 128 (FIG. 3) for protecting the drive assembly from dust and debris, and/or preventing dust and debris from the drive assembly from contaminating samples during assaying.

Figure 11:
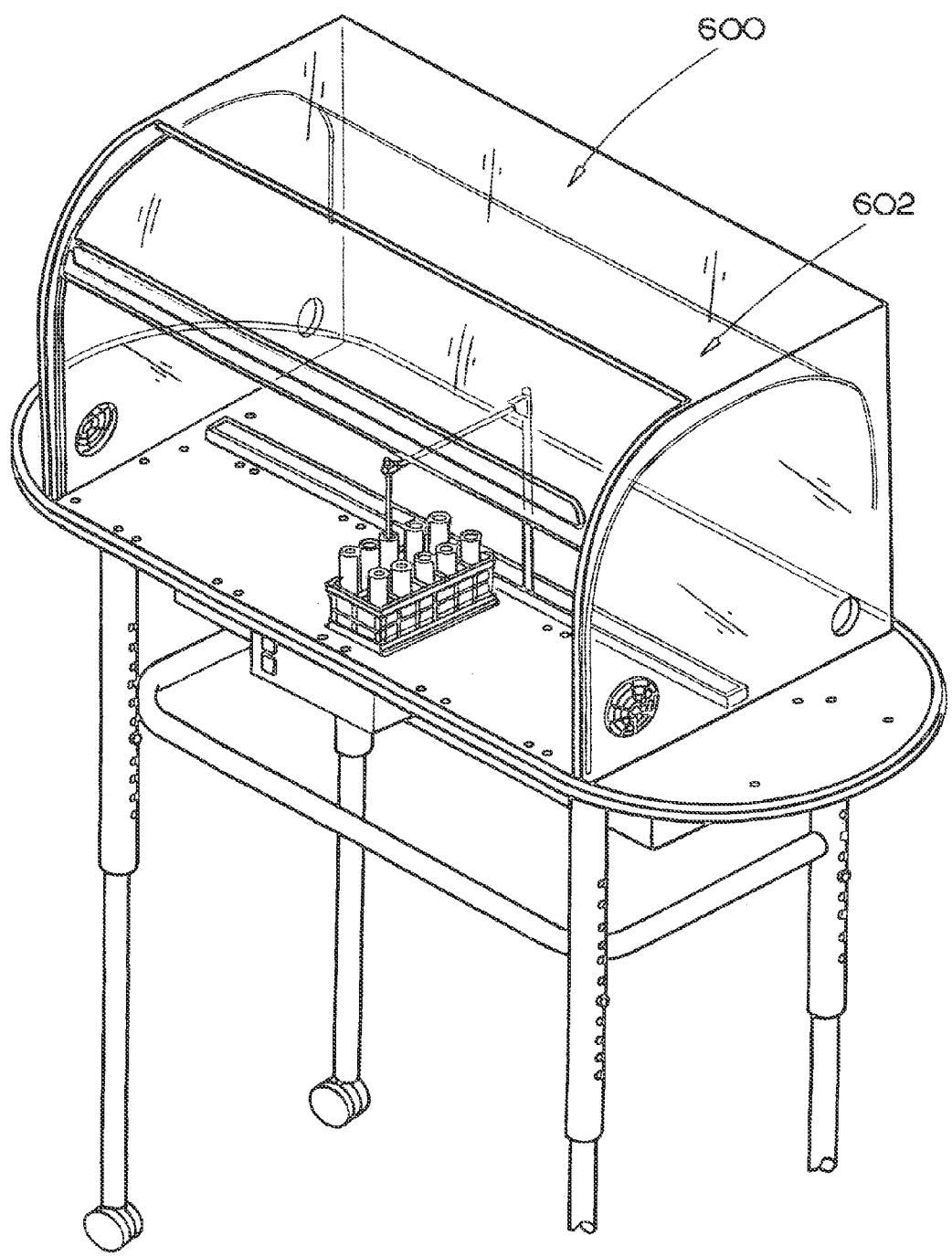
FIG. 11 is an isometric view illustrating an automated sampling or dispensing device in accordance with example implementations of the present disclosure, where the device is contained within a hood.

FIG. 11 illustrates automated sampling device 600 completely enclosed within a hood 602. Use of the hood allows the operations inside the hood to be isolated from the outside environment. The area within the hood may be ventilated to prevent the entry of contaminates such as bacteria or air-borne substances. In one specific implementation, the air drawn into the enclosure is passed through a high efficiency particulate air (HEPA) filter. Further, processing of samples which contain hazardous chemicals within a hood allows such samples to be processed without further exposing the user to such chemicals during processing.

Referring generally to FIGS. 12 through 19, various implementations of an enclosure for an automated sampling/dispensing device are provided. In general, the enclosure includes at least one support member. The support member is generally perpendicular to a support surface on which the automated sampling/dispensing device is mounted. Further, a lid is mechanically coupled to the at least one support member for covering the support surface on which the automated sampling/dispensing device is mounted. Additionally, at least one flexible sheet is operationally coupled to at least one of the lid or the at least one support member. The at least one support member may provide support to both the lid as well as the at least one flexible sheet. The at least one support member, lid, and at least one flexible sheet enclose the automated sampling device while allowing access to the device by retracting the at least one flexible sheet.

The presently described example enclosures may minimize user exposure to the enclosed samples by allowing the containment of potentially hazardous chemicals within such enclosure. Further, the use of at least one flexible panel allows the enclosure to be shipped efficiently, as the enclosure may be disassembled into smaller pieces and thus be shipped in a smaller box when compared to enclosures with non-flexible panels/doors. Moreover, the use of the at least one flexible panel allows the enclosure to be shaped to accommodate varying shaped automated sampling and or dispensing devices and assemblies.

Figure 12:
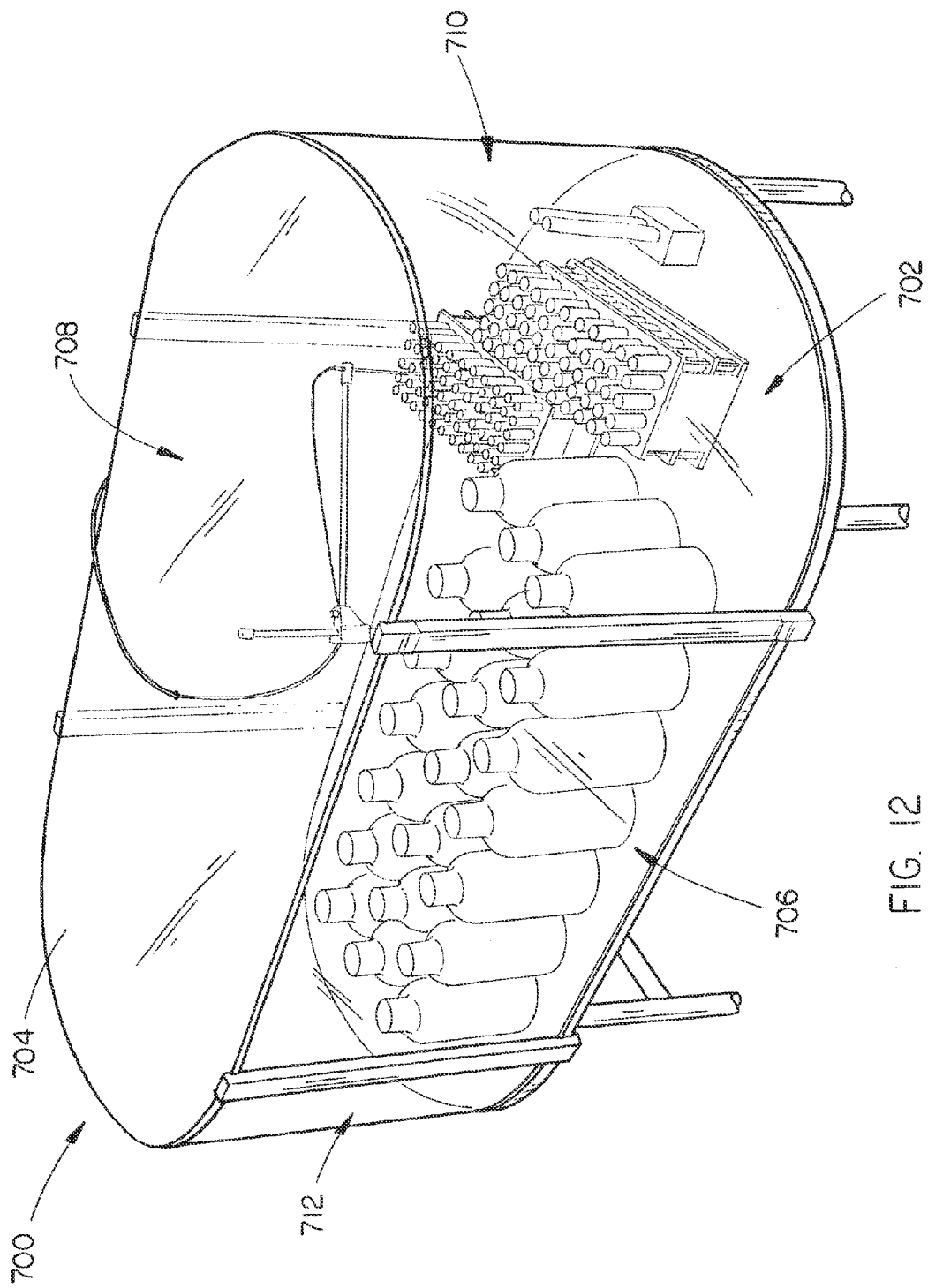
FIG. 12 is an isometric view illustrating an automated sampling or dispensing enclosure in accordance with example implementations of the present disclosure, where the enclosure includes two flexible sheets.

Referring to FIG. 12, an enclosure 700 for an automated sampling/dispensing device is provided in which the enclosure 700 surrounds an automated sampling/dispensing device mounted to a circular support surface 702. In an example implementation, the enclosure 700 includes a lid 704 for covering the support surface 702 on which the automated sampling/dispensing device is mounted. In such implementation, the lid 704 is generally equivalent in shape and size to that of the support surface 702 allowing the entire support surface 702 to be enclosed and available for use by a user. Further, an aperture for allowing the automated sampling/dispensing device to be connected with devices external to the enclosure may be defined within the lid. As illustrated in FIG. 12, an aperture defined within the lid 704 of the enclosure 700 allows a supply tube to the automated sampling/dispensing device to be connected with external laboratory analysis equipment. In another implementation, the enclosure 700 is designed to be airtight, allowing the enclosure 700 to contain potentially hazardous chemicals without requiring unnecessary exposure to laboratory personnel during sample preparation or analysis.

As illustrated in FIG. 12, the enclosure 700 includes a first support member 706 and a second support member 708. The first and second support members 706 and 708 are generally perpendicular to a support surface 702 on which the automated sampling/dispensing device is mounted. For example, as illustrated in FIG. 12, the first support member 706 and the second support member 708 are centered generally one hundred and eighty degrees (180°) opposite from one another. Moreover, such support members may be mechanically coupled to the lid 704 of the enclosure 700 as well as to the support surface 702. For instance, fasteners such as screws, bolts, nuts, and so forth may be used to fasten the support members to the lid and support surface. In an implementation, all fasteners are either metal-free or coated with an inert plastic coating to prevent interaction of such fasteners with chemical reagents or other substances being used with the automated sampling/dispensing device. In an additional implementation, an aperture may be formed within one or both of the support members to allow tubes, cords, and so forth to be connected to the automated sampling dispensing device contained within the enclosure as well as to external devices (e.g., laboratory analysis equipment), power sources, and so forth. It is contemplated that the lid 704 as well as the first support member 706 and the second support member 708 may be formed of inert, light-weight material including Plexiglas® (generically known as Lucite or polymethyl methacrylate.)

In additional implementations, as illustrated in FIG. 12, a first flexible sheet 710 and a second flexible sheet 712 are operationally coupled to at least one of the lid 708 or the first support member 706 or the second support member 708. In an implementation, the first flexible sheet 710 includes a first end and a second end. The first end of the first flexible sheet 710 includes a finished edge while the second end of the first flexible sheet 710 is fixedly coupled to the second support member 708. For example, the first end of the flexible sheet 710 is finished with a hardened-plastic cover which extends substantially along the length of the first end of the first flexible sheet 710. In addition, at least one guide member is attached to the first end of the first flexible sheet 710 to allow position of the first flexible sheet to be varied.

Figure 13:
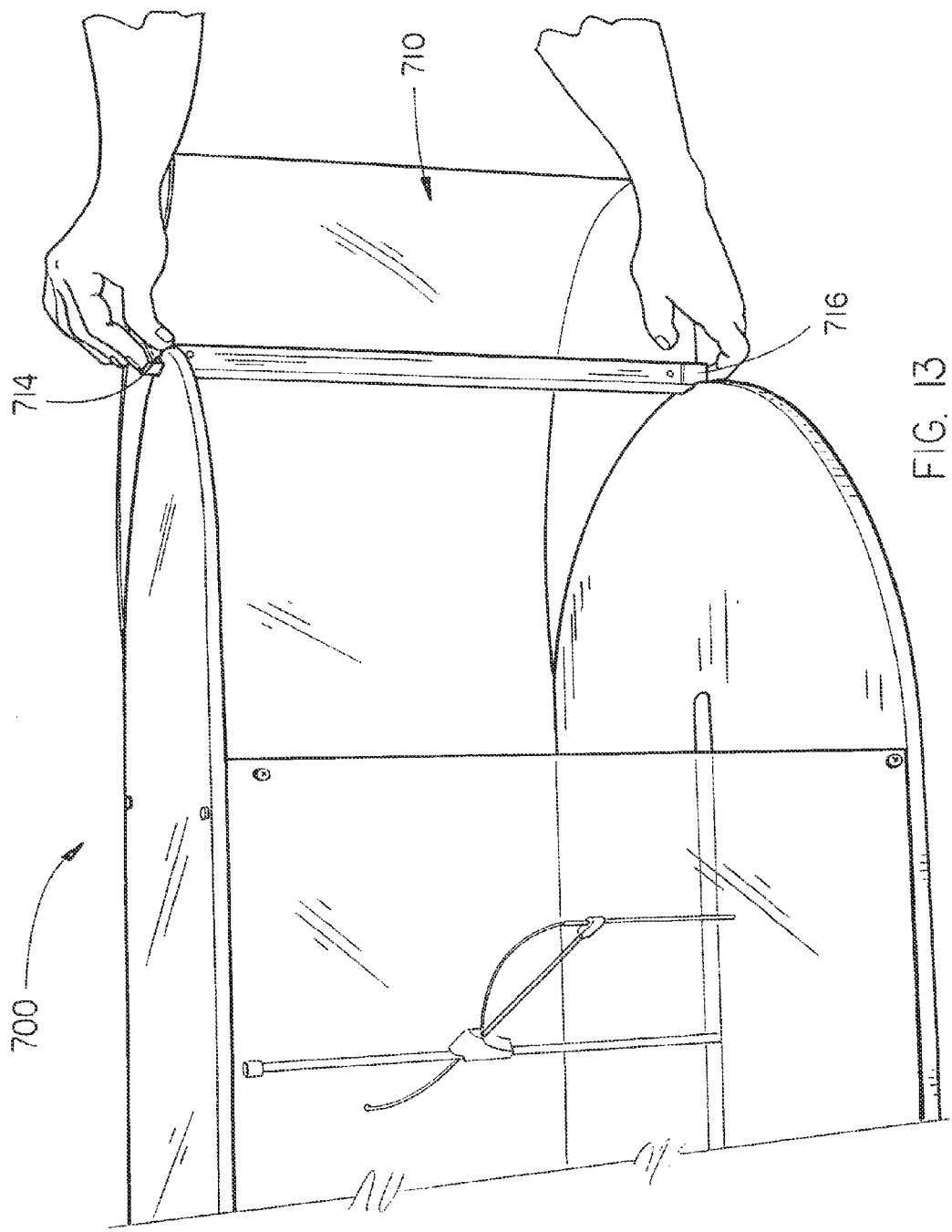
FIG. 13 is a partial front view of the automated sampling or dispensing device enclosure as illustrated in FIG. 12, where one of the flexible sheets of the enclosure is retracted.
Figure 14:
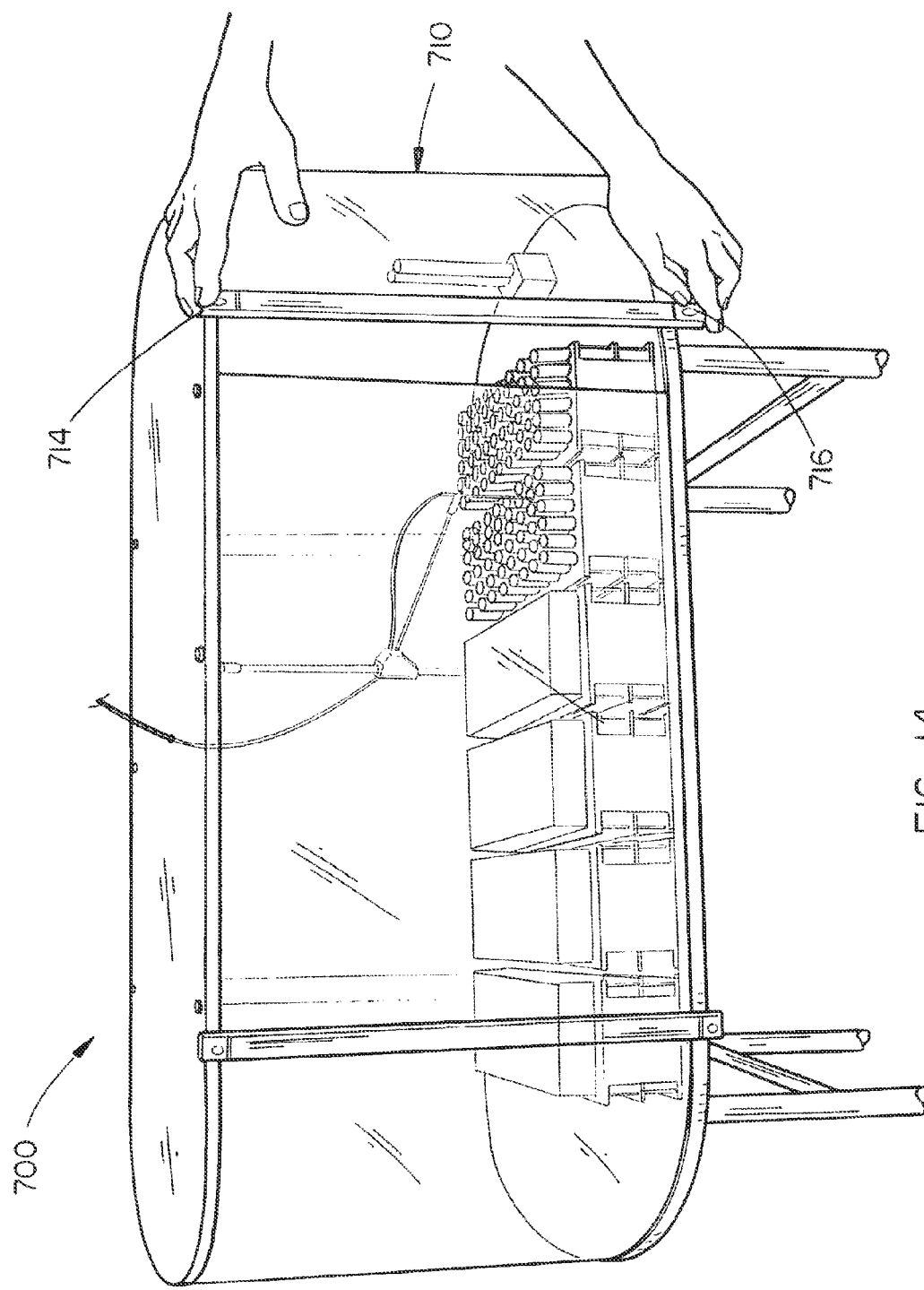
FIG. 14 is a front view of the automated sampling or dispensing device enclosure as illustrated in FIG. 12, where the mechanism of fastening a flexible side shut is demonstrated.

As illustrated in FIGS. 13 and 14, the first end of the first flexible sheet 710 includes a first guide member 714 and a second guide member 716 to allow a user to slide the first flexible sheet 710 along an edge of the support surface 702. In an implementation, the first guide member 714 and the second guide member 716 are press-fit latches allowing a user to secure the flexible sheet at multiple positions along the edge or side of the support surface. For example, a user may release the flexible sheet by applying pressure to the press-fit latches. As illustrated in FIG. 14, a flexible sheet may be moved from a first position to a second position by guiding the first guide member 714 along the edge of the lid 704 while the second guide member is detached from the support surface 710. It is contemplated that additional mechanisms may be employed to guide and secure the flexible sheet at various positions, including fasteners such as clips, pressure-sensitive screws, and so forth. It is further contemplated that a channel may be formed within the support surface to provide an area in which a guide member may slide and be secured.

In the present implementation, the second flexible side 712 includes a first end and a second end. The first end of the second flexible sheet 712 includes a finished edge while the second end of the second flexible sheet 712 is fixedly coupled to the second support member 708. For example, the first end of the second flexible sheet 712 is finished with a hardened-plastic (e.g., Plexiglas®) cover which extends substantially along the length of the first end of the second flexible sheet 712. In addition, at least one guide member is attached to the first end of the second flexible sheet 712 to allow position of the first flexible sheet to be varied. For instance, the first end of the second flexible sheet 712 may include a first guide member 714 and a second guide member 716 to allow a user to slide the second flexible sheet 712 along an edge or side of the support surface 702. In an implementation, the first guide member 714 and the second guide member 716 are press-fit latches allowing a user to secure the flexible sheet at multiple positions along the edge or side of the support surface. It is contemplated that additional mechanisms may be employed to guide and secure the flexible sheet at various positions, including fasteners such as clips, pressure-sensitive screws, and so forth.

Figure 15:
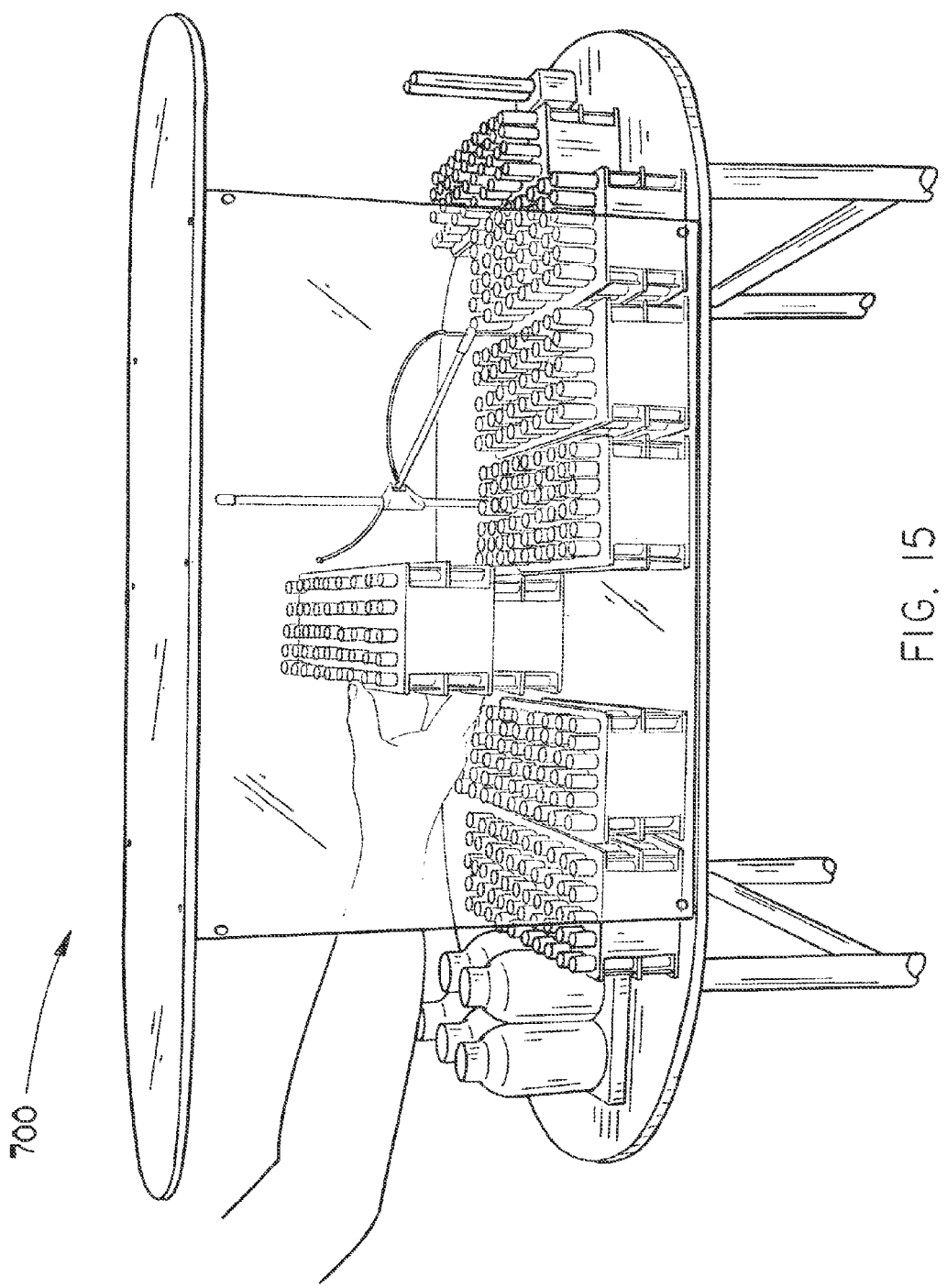
FIG. 15 is a front view of the automated sampling or dispensing device enclosure as illustrated in FIG. 12, where the flexible sheets have been removed.

Referring to FIG. 15, the first and second flexible sheets have been removed to allow access to the support surface 702. In an implementation, the first and second flexible sheets are detachable. The detachable features of such sheets allow a user to load or remove samples efficiently from the support surface 702 so that a user does not have to reposition the sheets in order to gain access to a support surface area. It is contemplated that one or both sheets may be removed depending upon the needs of the user.

Figure 16:
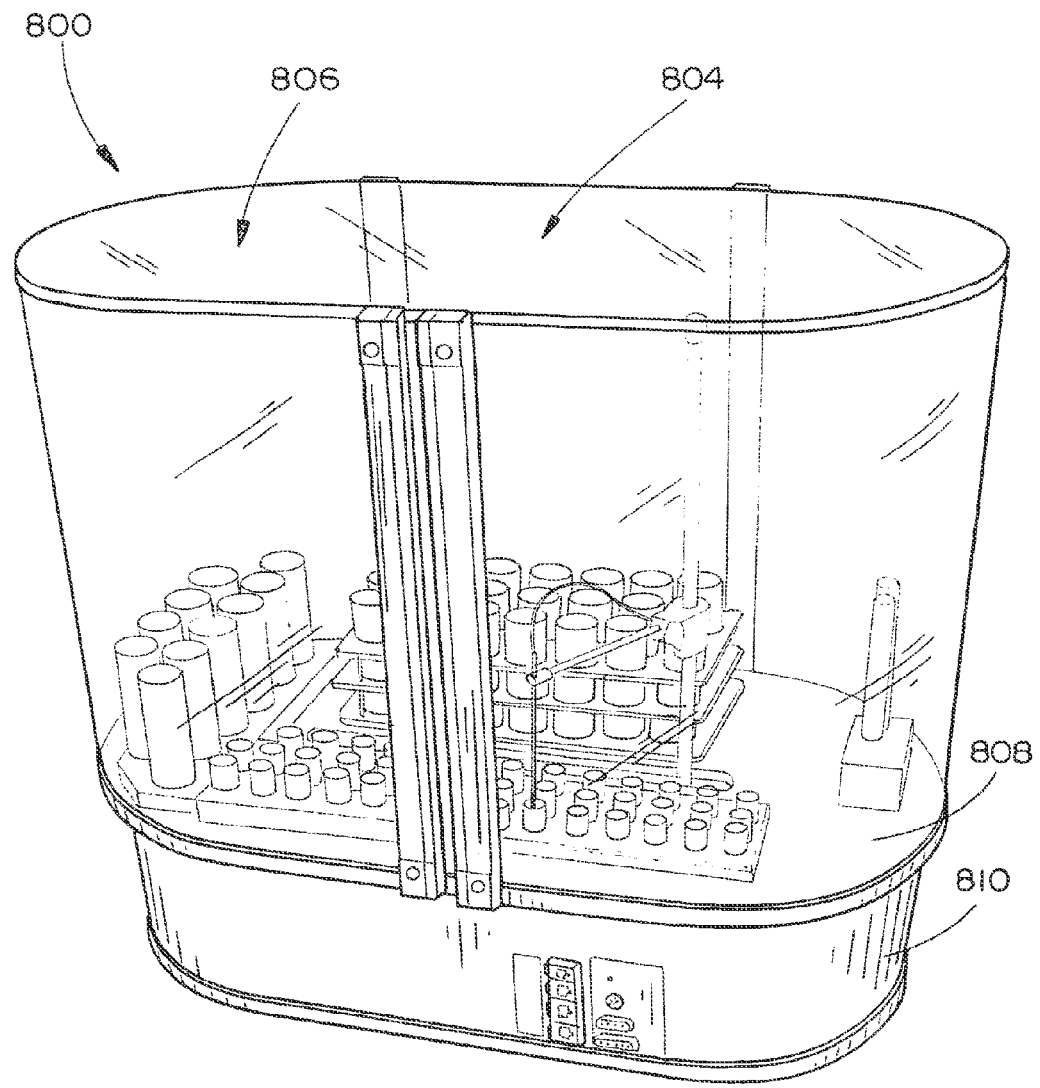
FIG. 16 is an isometric view illustrating an enclosure for a bench top automated sampling or dispensing device in accordance with example implementations of the present disclosure, where the enclosure includes flexible sheets which are in a closed position.
Figure 17:
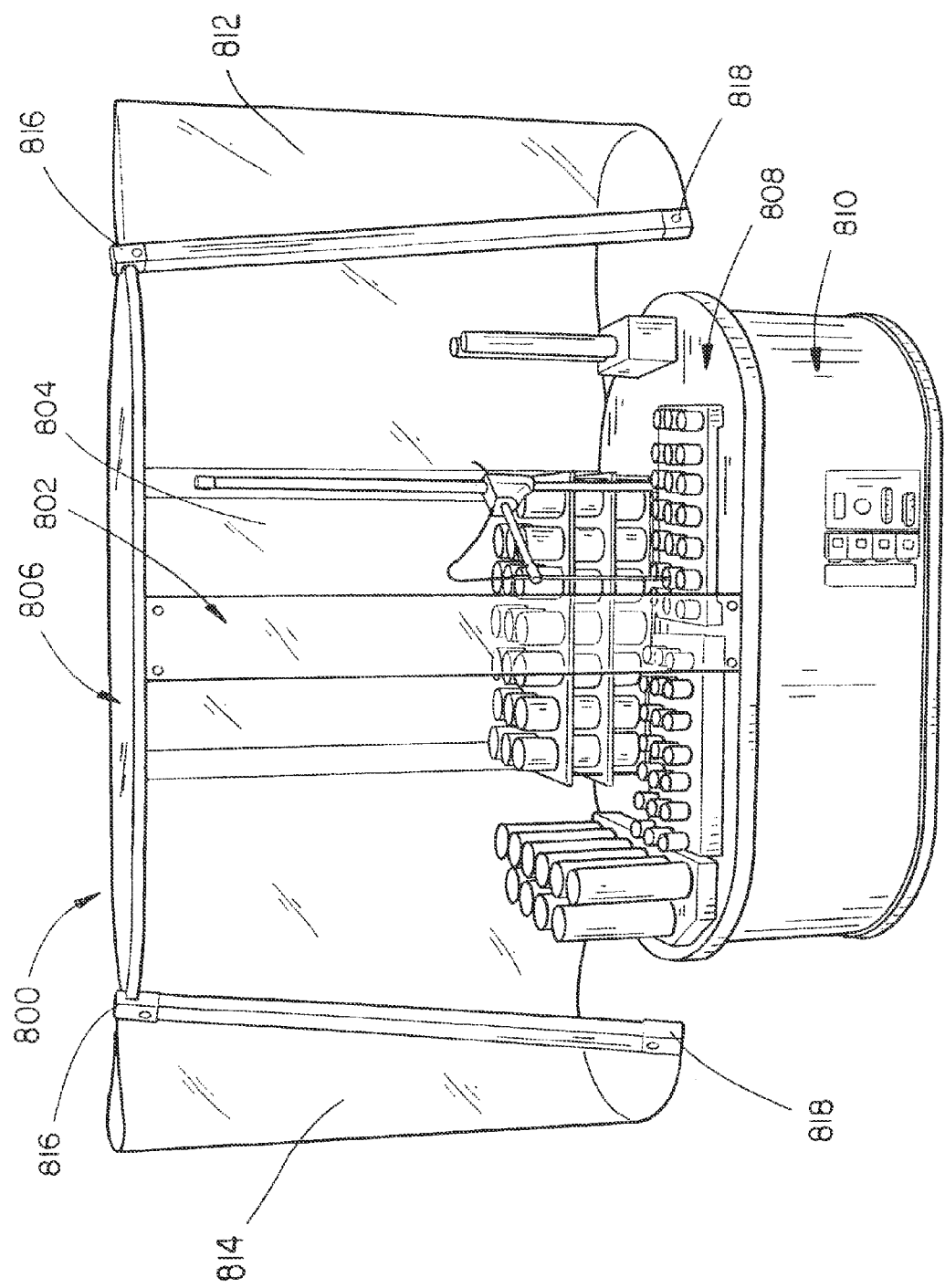
FIG. 17 is a front view of the enclosure for the bench top automated sampling or dispensing device as illustrated in FIG. 16, where the flexible sheets are in an open position.

Referring to FIGS. 16 and 17, an additional example enclosure for enclosing an automated sampling/dispensing device is provided in which the automated sampling/dispensing device is a bench-top automated sampling dispensing device. As illustrated in FIGS. 16 and 17, an enclosure 800 for a bench-top automated sampling dispensing device is configured in a similar manner as the enclosure 700 for a table-top automated sampling/dispensing device. The enclosure 800 includes a first support member 802 and a second support member 804 for supporting a lid 806. In an example implementation, the lid 806 covers a support surface 808 secured to a base 810 of the bench-top automated sampling/dispensing device. In such implementation, the lid 806 is generally equivalent in shape and size to that of the support surface 808, allowing the entire support surface 808 to be enclosed and available for use by a user. Further, the first 802 and second 804 support members are generally perpendicular to the support surface 808.

As illustrated in FIGS. 16 and 17, the first support member 802 and the second support member 804 are centered generally one hundred and eighty degrees (180°) opposite from one another. For example, the first support member 802 is positioned on the front side of the automated sampling/dispensing device (the front side defined as the side including a user power control panel) while the second support member 804 is positioned generally opposite the first support member 802 (e.g., to the rear side of the automated sampling/dispensing device). Moreover, such support members may be mechanically coupled to the lid 806 of the enclosure 800 as well as to the support surface 808. For instance, fasteners such as screws, bolts, nuts, and so forth may be used to fasten the support members to the lid and support surface. In an implementation, all fasteners are either metal-free or coated with an inert plastic coating to prevent interaction of such fasteners with chemical reagents or other substances being used with the automated sampling/dispensing device.

It is contemplated that the lid 806 as well as the first support member 802 and the second support member 804 may be formed of inert, light-weight material including Plexiglas®. It is further contemplated that the enclosure 800 may include an aperture within the lid or at least one of the support members allowing for the automated sampling/dispensing device to be connected with devices external to the enclosure. For example, an aperture may be defined within the lid for allowing a supply tube to the automated sampling/dispensing device to be connected with external laboratory analysis equipment. In another implementation, the enclosure 800 is designed to be airtight allowing the enclosure to contain potentially harmful chemicals without requiring unnecessary exposure to laboratory personal during sample preparation or analysis.

In additional example implementations, as illustrated in FIG. 17, a first flexible sheet 812 and a second flexible sheet 814 are coupled to at least one of the lid 806 or the first support member 802 or the second support member 804. In an implementation, each flexible sheet includes a first and second end. The first end of each flexible sheet includes a finished edge while the second end of each flexible sheet is fixedly coupled to the second support member 804. For example, the first end of the flexible sheet 812 is finished with a hardened-plastic cover (e.g., Plexiglas®) which extends substantially along the length of the first end of the first flexible sheet 812.

In further example implementations, at least one guide member is attached to the first end of each flexible sheet to allow the position of each flexible sheet to be varied. As illustrated in FIG. 17, the first end of each flexible sheet includes a first guide member 816 and a second guide member 818 to allow a user to slide each sheet along an edge of the lid 806 or support surface 808. In an implementation, the first guide member 816 and the second guide member 818 are press-fit latches allowing a user to secure the flexible sheet at multiple positions along the edge or side of the lid or support surface. For example, a user may release the flexible sheet by applying pressure to the press-fit latches. As illustrated in FIG. 17, a flexible sheet may be moved from a first position to a second position by guiding the first guide member 816 along the edge of the lid 806 while the second guide member 818 is detached from the support surface 808. It is contemplated that additional mechanisms may be employed to guide and secure the flexible sheet at various positions, including fasteners such as clips, pressure-sensitive screws, and so forth. It is further contemplated that a channel may be formed within the support surface to provide an area in which a guide member may slide and be secured.

It is contemplated that the first and second flexible sheets may be detachable. The detachable features of such sheets allow a user to load or remove samples efficiently from the support surface 808 so that a user does not have to reposition the sheets in order to gain access to a support surface area. It is contemplated that one or both sheets may be removed depending upon the needs of the user.

Figure 18:
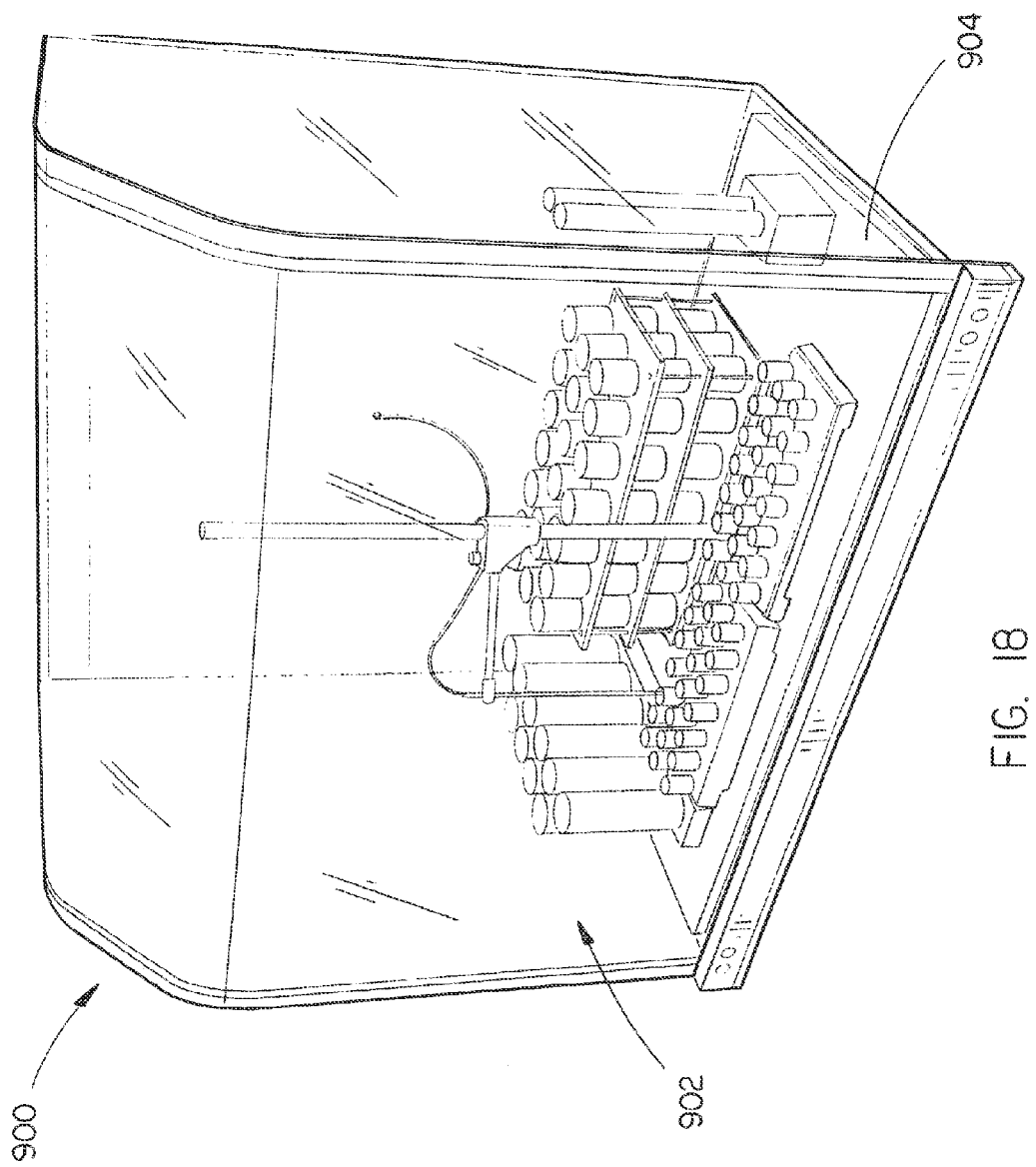
FIG. 18 is an isometric view illustrating an enclosure for an automated sampling or dispensing device in accordance with example implementations of the present disclosure, where the enclosure includes a single flexible front sheet.
Figure 19:
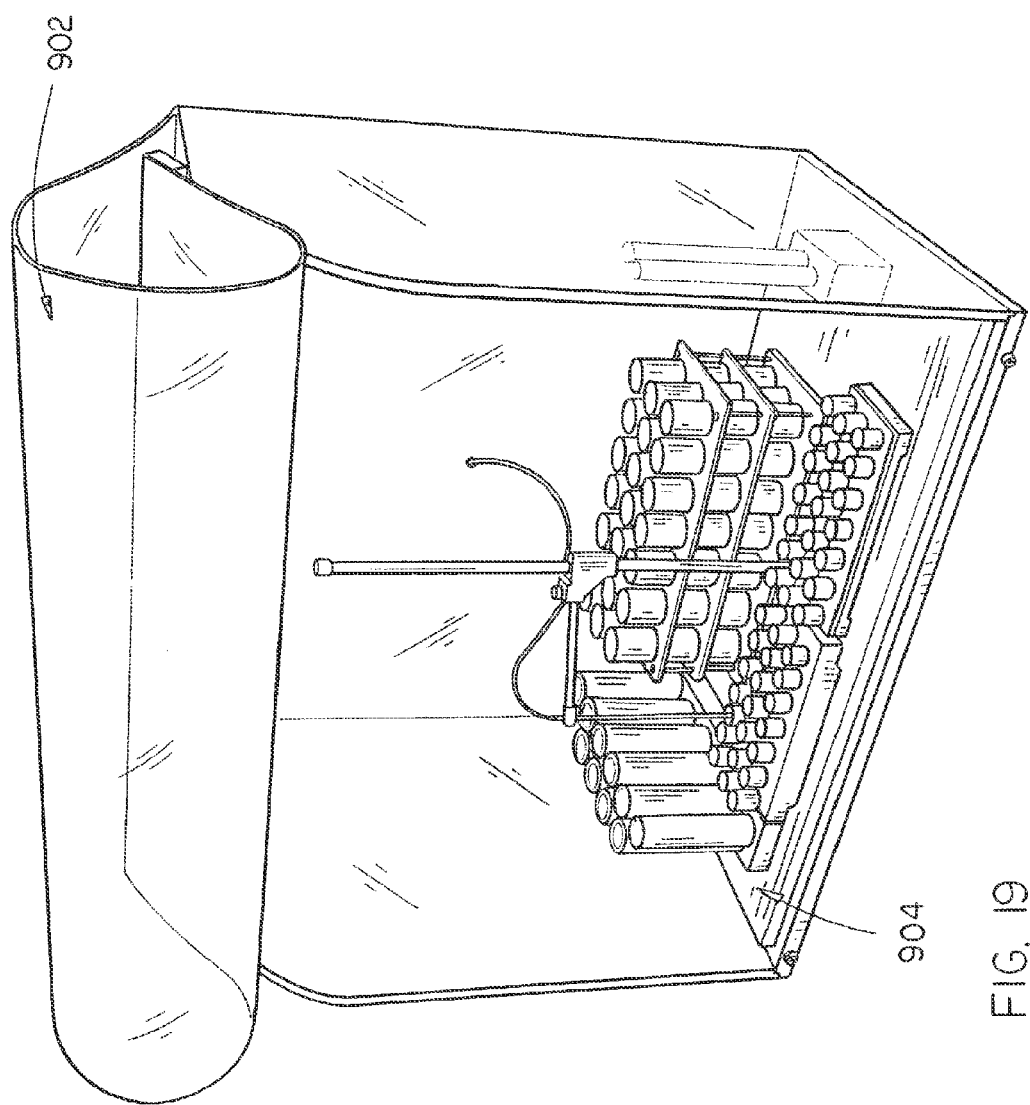
FIG. 19 is an isometric view of the enclosure for the automated sampling or dispensing device as illustrated in FIG. 18, where the front sheet is retracted allowing access to the device.

Referring to FIGS. 18 and 19, a further example enclosure 900 for enclosing an automated sampling/dispensing device is provided in which the enclosure 900 includes a single flexible sheet or panel 902. As illustrated in FIGS. 18 and 19, the enclosure 900 includes a plurality of support walls and a single flexible sheet 902 for enclosing the automated sampling/dispensing device mounted on a support surface 904. For example, the enclosure 900 may include three support walls and the single flexible sheet 902. In such example, a first side support wall and a second side support wall provide support to a rear support wall in which the rear support wall is secured to an edge of the first side support wall and an edge of the second side support wall. The rear support wall is generally opposite to that of the front of the enclosure (e.g., where the front of the enclosure includes the flexible sheet and is used to gain access to the automated sampling/dispensing device). The first and second side support walls are configured to allow the flexible sheet to be rolled along an outer edge of the first side support wall and an outer edge of the second side support wall. It is contemplated that an aperture may be defined within at least one of the plurality of walls for allowing the enclosed apparatus to be connected with external devices or power sources.

With continued reference to FIGS. 18 and 19, the single flexible sheet 902 includes a first and second edge. The first end of the flexible sheet 902 includes a finished edge while the second end of the flexible sheet 902 is fixedly coupled to the rear support wall. For example, the first end of the flexible sheet 902 is finished with a hardened-plastic cover which extends substantially along the length of the first end of the flexible sheet 902. To gain access to the interior of the enclosure 900, the single flexible sheet 902 may be retracted with a first end of the first edge of the single flexible sheet 902 being secured to the outer edge of the first side support wall and a second end of the first edge being secured to the outer edge of the second side support wall. It is contemplated that various mechanisms may be employed to secure the first edge of the flexible sheet 902 to the side support edges including press fit latches, clips, screws, and so forth. In addition, the enclosure 900 may be mounted to an automated sampling/dispensing device for laboratory analysis equipment in which the enclosure may be positioned to enclose such device by securing the enclosure to a support area supporting the device. Moreover, the single flexible sheet may be detachable allowing a user access to the entire support surface area as well as to the over-head support surface area.

Although the presently described enclosure focuses upon the use of such enclosure with an automated sampling/dispensing device, it is contemplated that such enclosure may be employed with a variety of laboratory equipment in accordance with the present disclosure. It is further contemplated that example enclosures may be ventilated to prevent the entry of contaminates such as bacteria or air-borne substances into the external environment. For instance, the air drawn into the enclosure can be passed through a HEPA filter.

Figure 20:
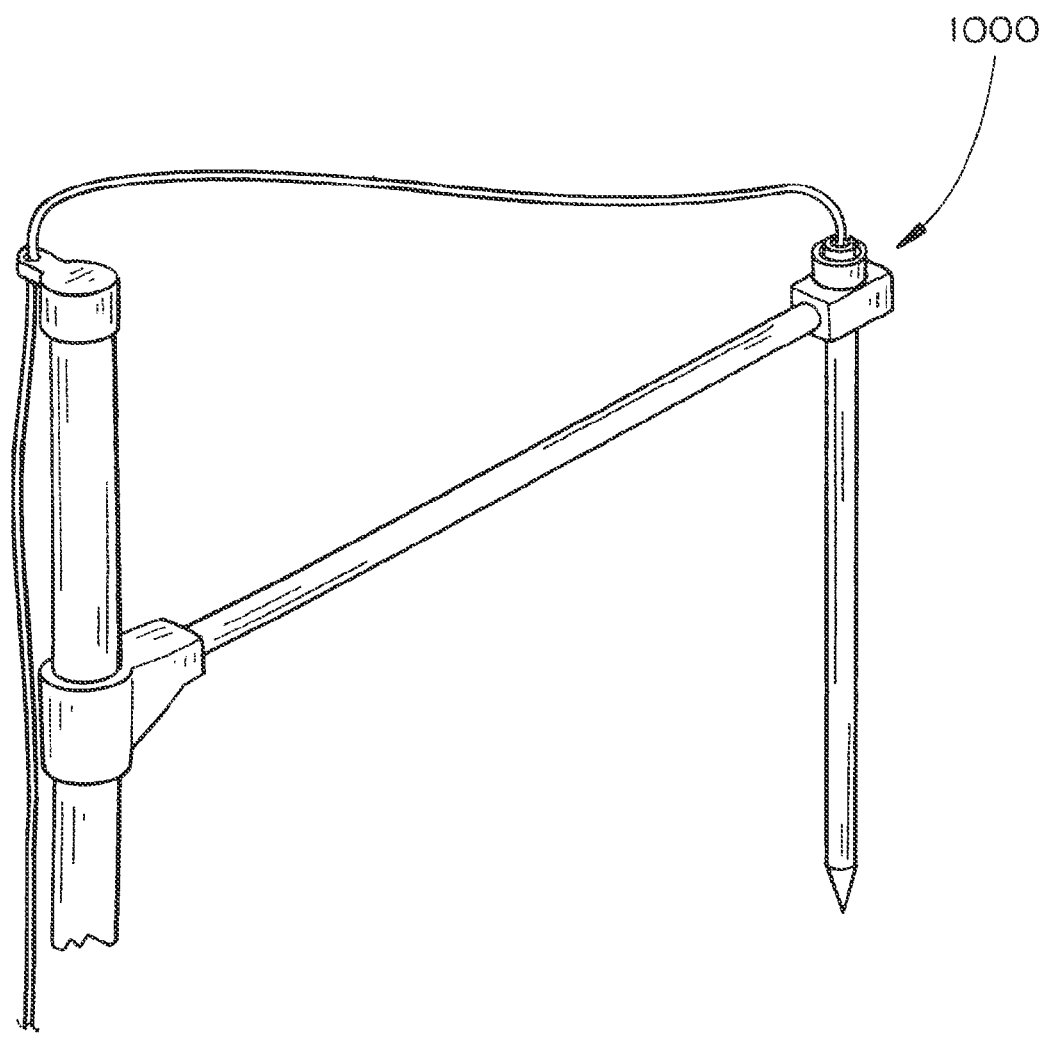
FIG. 20 is a partial isometric view illustrating a sample arm assembly for an automated sampling or dispensing device in accordance with example implementations of the present disclosure, where the sample arm assembly includes a dampening device for dampening vibrations generated during use.

Referring now to FIG. 20, a sample arm assembly for an automated sampling or dispensing device in accordance with an example implementation of the present disclosure is provided in which the sample arm assembly includes a dampening device for dampening vibrations generated during use. As illustrated in FIG. 20, the sample arm assembly includes the sample probe 114 allowing samples to be dispensed or removed from various sample vessels. A dampening device 1000 is positioned around a first end of the sample probe 114 which is generally opposite to a second end of the sample probe 114, the second end of the sample probe making contact with sample and sample vessels. The dampening device 1000 allows the vibrations generated during operation of the automated sampling/dispensing device to be minimized by moving out of phase with the automated sampling/dispensing device sample probe. The minimization of the vibrations allows accurate positioning of the sample probe and thus minimizes the possibility of sample cross-contamination without requiring the speed of the automated sampling/dispensing device to be reduced.

Figure 21:
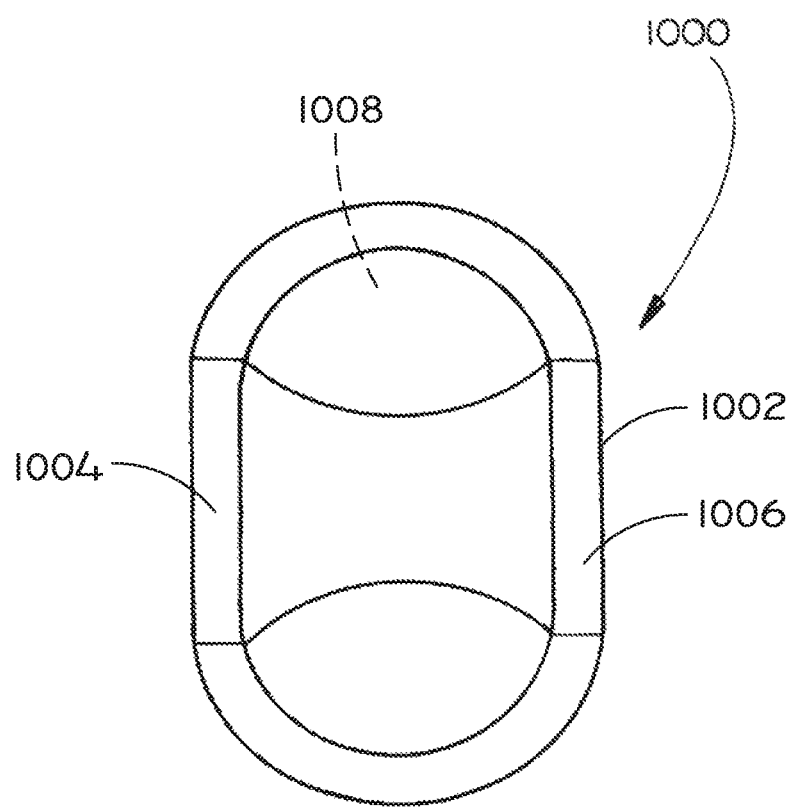
FIG. 21 is an isometric view of a dampening device for an automated sampling or dispensing device in accordance with example implementations of the present disclosure.

In an example implementation, the dampening device 1000 includes a body 1002 with a plurality of walls. As illustrated in FIG. 21, the body 1002 is generally cylindrical and includes a first end and a second end. Further, a first opening 1004 is defined within the first end and a second opening 1006 is defined within the second end. Further, in an implementation, the body 1002 comprises an inner diameter greater than an outer diameter of an automated sampling/dispensing device sample probe. For example, for a sample probe with a diameter of three millimeters (3 mm), the inner diameter of the cylindrical body can be approximately six millimeters (6 mm). The use of a dampening device with an inner cylindrical diameter approximately two times that of the sample probe allows the device to be placed loosely around the first end of the sample probe. During operation, the dampening device is allowed to move out of phase with the automated sampling/dispensing device sample probe allowing sample probe vibrations to be dampened.

Figure 22B:
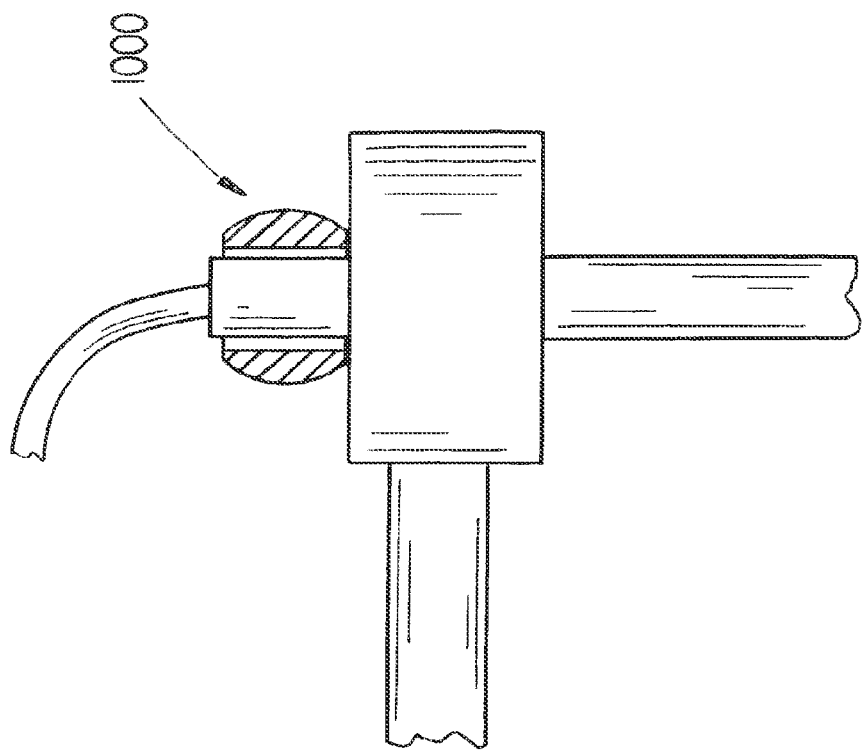
FIG. 22B is a partial side view of an automated sampling or dispensing device in accordance with example implementations of the present disclosure, where a cross-sectional view of an additional example dampening device is provided.
Figure 22A:
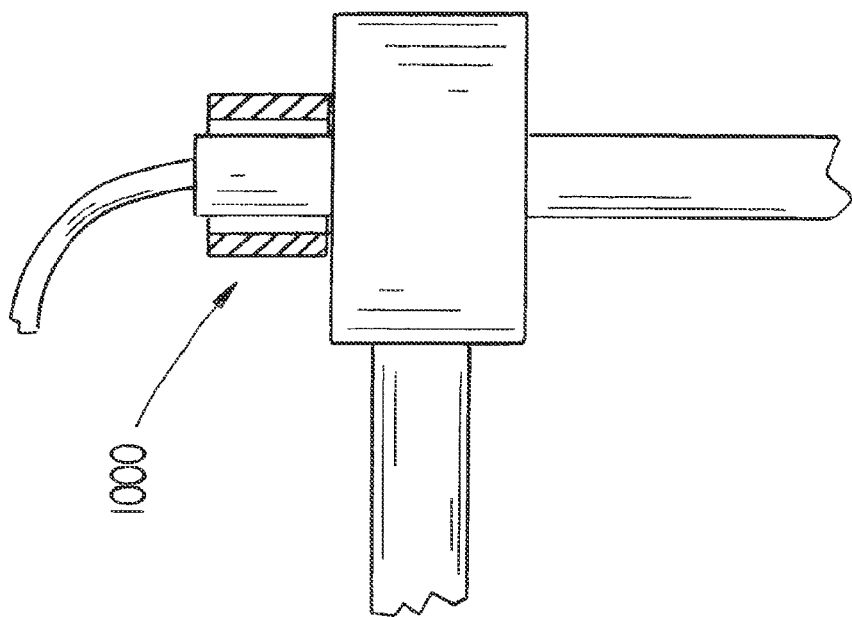
FIG. 22A is a partial side view of an automated sampling or dispensing device in accordance with example implementations of the present disclosure, where a cross-sectional view of an example dampening device is provided.

It is contemplated that the dampening device may be composed of metal-free, inert material, including plastic. The use of metal-free, inert materials allows the dampening device to be lightweight and removes the possibility of the device reacting with chemicals or other substance. It is further contemplated that the size and shape of the dampening device may vary depending upon the size and shape of the sample probe on which it is to be positioned. For example, as illustrated in FIGS. 22A and 22B, the inner diameter of the dampening device may be square or spherical, respectively.

In an additional example implementation, the body 1002 of the dampening device 1000 includes a slit extending along the length of the cylindrical body for allowing the dampening device 1000 to be positioned around the first end of the sample probe 114 which is generally opposite to the second end of the sample probe 114 which makes contact with a sample. The slit allows the dampening device 1000 to be positioned without requiring the user to slide the device over additional components of the automated sampling/dispensing device. For example, the slit is of a width to allow the dampening device 1000 to be positioned around the first end of the sample probe 114 and remain around the first end of the sample probe 114 during sample probe operation.

In implementations, the first end of the sample probe 114 and/or the dampening device 1000 can be constructed using material and/or equipment configured to produce a magnetic field so that the first end of the sample probe 114 and the dampening device 1000 are magnetically attracted to one another. For example, the first end of the sample probe 114 and/or the dampening device 1000 can include one or more permanent magnetic materials 131 and/or 1008 (e.g., material that is magnetized and creates its own magnetic field), such as rare earth magnets, and so forth. The first end of the sample probe 114 and/or the dampening device 1000 can also include one or more ferromagnetic and/or ferrimagnetic materials (e.g., materials that are strongly attracted to magnets), such as iron, nickel, cobalt, rare earth metal alloys, minerals such as lodestone, and so forth. Additionally, the first end of the sample probe 114 and/or the dampening device 1000 can include an electromagnet (e.g., a material configuration that acts as a magnet when an electric current passes therethrough), such as a coil of wire. In some instances, a coil of wire can be wrapped around a ferromagnetic material (e.g., steel) to enhance the magnetic field produced by the coil.

Although the subject matter has been described in language specific to structural features and/or process operations, it is to be understood that the subject matter defined in the appended claims is not necessarily limited to the specific features or acts described above. Rather, the specific features and acts described above are disclosed as example forms of implementing the claims.

What is claimed is:

1. A dampening device for an automated sampling and dispensing device, comprising:
   a cylindrical body, the cylindrical body including a first end and a second end, a first opening being defined within the first end and a second opening being defined within the second end allowing the cylindrical body to be positioned around an automated sampling and dispensing device sample probe; the cylindrical body including an inner diameter greater than an outer diameter of the automated sampling and dispensing device sample probe, the inner diameter of the cylindrical body partially contacting the outer diameter of the sample probe,
   the cylindrical body moving out of phase with the automated sampling/dispensing device sample probe allowing sample probe vibrations to be dampened during operation, the dampening device comprising at least one of a permanent magnetic material, a ferromagnetic material, a ferrimagnetic material, or an electromagnet.

2. The dampening device as claimed in claim 1, wherein the dampening device is configured to be positioned around a first end of the sample probe which is generally opposite to a second end of the sample probe which makes contact with a sample.

3. The dampening device as claimed in claim 1, wherein the dampening device is at least partially formed of plastic.

4. The dampening device as claimed in claim 1, wherein the dampening device is at least partially formed of metal-free material.

5. A dampening device for an automated sampling/dispensing device, comprising:
   a body, the body including a plurality of walls, a first end and a second end, a first opening being defined within the first end and a second opening being defined within the second end allowing the body to be positioned around an automated sampling and dispensing device sample probe; the body including an inner diameter greater than an outer diameter of an automated sampling and dispensing device sample probe, the inner diameter of the body partially contacting the outer diameter of the sample probe,
   wherein the dampening device is configured to be positioned around the automated sampling and dispensing device sample probe so that during operation the device moves out of phase with the automated sampling/dispensing device sample probe allowing sample probe vibrations to be dampened, the dampening device comprising at least one of a permanent magnetic material, a ferromagnetic material, a ferrimagnetic material, or an electromagnet.

6. The dampening device as claimed in claim 5, wherein the dampening device is configured to be positioned around a first end of the sample probe which is generally opposite to a second end of the sample probe which makes contact with a sample.

7. The dampening device as claimed in claim 5, wherein the plurality of walls are configured to form a cylindrical body.

8. The dampening device as claimed in claim 5, wherein the inner diameter of the body is cylindrical in shape.

9. The dampening device as claimed in claim 5, wherein the dampening device is at least partially formed of plastic.

10. The dampening device as claimed in claim 5, wherein the dampening device is at least partially formed of metal-free material.

11. An automated sampling and dispensing device including a dampening device, comprising:
    a support surface for supporting a sample holder, the sample holder configured for holding a sample vessel;
    a sample arm assembly for supporting a sample probe, the sample arm assembly including a z-axis support and a sample probe support arm, the sample arm assembly comprising at least one of a permanent magnetic material, a ferromagnetic material, a ferrimagnetic material, or an electromagnet;
    a drive assembly coupled to the z-axis support of the sample arm assembly for powering and positioning the sample arm assembly, the drive assembly causes the sample arm assembly to move in translation along the x-axis, in translation along an axis coaxial with the z-axis support, and radially about the z-axis; and
    a dampening device operationally coupled to the sample arm assembly for dampening vibrations of the sample arm assembly during operation, the dampening device including a cylindrical body, the cylindrical body including a first end and a second end, a first opening being defined within the first end and a second opening being defined within the second end allowing the cylindrical body to be positioned around the sample probe; the cylindrical body including an inner diameter greater than an outer diameter of the sample probe, the inner diameter of the cylindrical body partially contacting the outer diameter of the sample probe,
    wherein the dampening device is configured to be positioned around the sample probe so that during operation the dampening device moves out of phase with the sample probe allowing sample probe vibrations to be dampened, the dampening device comprising at least one of a permanent magnetic material, a ferromagnetic material, a ferrimagnetic material, the dampening device and the sample arm assembly configured to be magnetically attracted to one another.

12. The automated sampling and dispending device including a dampening device as claimed in claim 11, wherein the dampening device is positioned around a first end of the sample probe which is generally opposite to a second end of the sample probe which makes contact with the sample vessel, the first end of the sample probe comprising the at least one of the permanent magnetic material, the ferromagnetic material, the ferrimagnetic material, or the electromagnet.

13. The automated sampling and dispending device including a dampening device as claimed in claim 11, wherein the dampening device is at least partially formed of plastic.

* * * * *